US011557036B2

(12) United States Patent
Liao et al.

(10) Patent No.: US 11,557,036 B2
(45) Date of Patent: Jan. 17, 2023

(54) METHOD AND SYSTEM FOR IMAGE REGISTRATION USING AN INTELLIGENT ARTIFICIAL AGENT

(71) Applicant: Siemens Healthcare GmbH, Erlangen (DE)

(72) Inventors: Rui Liao, Princeton Junction, NJ (US); Shun Miao, Bethesda, MD (US); Pierre de Tournemire, Nancy (FR); Julian Krebs, Moers (DE); Li Zhang, Princeton, NJ (US); Bogdan Georgescu, Princeton, NJ (US); Sasa Grbic, Plainsboro, NJ (US); Florin Cristian Ghesu, Princeton, NJ (US); Vivek Kumar Singh, Princeton, NJ (US); Daguang Xu, Princeton, NJ (US); Tommaso Mansi, Plainsboro, NJ (US); Ali Kamen, Skillman, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 331 days.

(21) Appl. No.: 16/861,353

(22) Filed: Apr. 29, 2020

(65) Prior Publication Data
US 2020/0258227 A1  Aug. 13, 2020

Related U.S. Application Data

(63) Continuation of application No. 15/587,094, filed on May 4, 2017, now abandoned.
(Continued)

(51) Int. Cl.
*G06K 9/00* (2022.01)
*G06T 7/00* (2017.01)
(Continued)

(52) U.S. Cl.
CPC .......... *G06T 7/0012* (2013.01); *A61B 5/7267* (2013.01); *G06T 7/30* (2017.01); *G06T 2207/20081* (2013.01)

(58) Field of Classification Search
CPC .......... G06T 3/0068; G06T 7/30; G06T 7/32; G06T 7/33; G06T 7/337; G06T 7/344;
(Continued)

(56) References Cited

U.S. PATENT DOCUMENTS 8,068,654 B2  11/2011  Barbu et al.
8,645,294 B1   2/2014  Owechko et al.
(Continued)

FOREIGN PATENT DOCUMENTS

CN  101916443 A  12/2010
CN  102385748 A   3/2012
(Continued)

OTHER PUBLICATIONS

Lotfi, Tayebeh, et al. "Improving probabilistic image registration via reinforcement learning and uncertainty evaluation." International workshop on machine learning in medical imaging. Springer, Cham, 2013. (Year: 2013).*
(Continued)

*Primary Examiner* — Avinash Yentrapati

(57) ABSTRACT

Methods and systems for image registration using an intelligent artificial agent are disclosed. In an intelligent artificial agent based registration method, a current state observation of an artificial agent is determined based on the medical images to be registered and current transformation parameters. Action-values are calculated for a plurality of actions available to the artificial agent based on the current state observation using a machine learning based model, such as a trained deep neural network (DNN). The actions correspond to predetermined adjustments of the transformation
(Continued)

parameters. An action having a highest action-value is selected from the plurality of actions and the transformation parameters are adjusted by the predetermined adjustment corresponding to the selected action. The determining, calculating, and selecting steps are repeated for a plurality of iterations, and the medical images are registered using final transformation parameters resulting from the plurality of iterations.

20 Claims, 16 Drawing Sheets

Related U.S. Application Data

(60) Provisional application No. 62/401,977, filed on Sep. 30, 2016, provisional application No. 62/344,125, filed on Jun. 1, 2016, provisional application No. 62/338,059, filed on May 18, 2016.

(51) Int. Cl.
    *G06T 7/30*     (2017.01)
    *A61B 5/00*     (2006.01)

(58) Field of Classification Search
    CPC .... G06T 7/35; G06T 7/37; G06T 7/38; G06T 2207/20081; G06T 7/0012; A61B 5/7267
    See application file for complete search history.

(56) References Cited

U.S. PATENT DOCUMENTS

| | | | |
|---|---|---|---|
| 9,042,614 | B2 | 5/2015 | Sun et al. |
| 9,495,746 | B2 | 11/2016 | Chou et al. |
| 9,547,902 | B2 | 1/2017 | Ionasec et al. |
| 2008/0211812 | A1 | 9/2008 | Barbu et al. |
| 2010/0067768 | A1 | 3/2010 | Ionasec et al. |
| 2016/0012592 | A1 | 1/2016 | Chou et al. |
| 2016/0093050 | A1 | 3/2016 | Kim et al. |
| 2017/0024634 | A1 | 1/2017 | Miao et al. |
| 2017/0032245 | A1 | 2/2017 | Osband et al. |
| 2017/0109881 | A1* | 4/2017 | Avendi ............... G06T 7/38 |
| 2019/0065848 | A1* | 2/2019 | Borrel ............... G06T 7/97 |
| 2020/0258227 | A1* | 8/2020 | Liao ............... A61B 5/7267 |

FOREIGN PATENT DOCUMENTS

| | | |
|---|---|---|
| CN | 102411780 A | 4/2012 |
| CN | 104835112 A | 8/2015 |

OTHER PUBLICATIONS

Mattes et al., "Nonrigid Multimodality Image Registration", Proceedings of the SPIE, 2001, vol. 4322, pp. 1609-1620.
Tieleman et al., Lecture 6.5-rmsprop: Divide the Gradient by a Running Average of its Recent Magnitude, COURSERA: Neural Networks for Machine Learning, 4, 2, 2012.
Thevenaz et al., "Optimization of Mutual Information for Multi resolution Image Registration", IEEE Transactions on Image Processing, Dec. 2000, vol. 9, No. 12, pp. 2083-2099.
Matsopoulos et al., "Automatic Retinal Image Registration Scheme Using Global Optimization Techniques", IEEE Transactions on Information Technology in Biomedicine, Mar. 1999, vol. 3, No. 1, pp. 47-60.
Rouet et al., "Genetic Algorithms for a Robust 3-D MR-CT Registration", IEEE Transactions on Information Technology in Biomedicine, Jun. 2000, vol. 4, No. 2, pp. 126-136.
Snoek et al., "Practical Bayesian Optimization of Machine Learning Algorithms", In Advances in Neural Information Processing Systems, 2012, 9 pgs.
Yuan, "Recent Advances in Trust Region Algorithms", Mathematical Programming, Oct. 1, 2014, pp. 1-26.
Miao et al., "System and Method for 3-D/3-D Registration between Non-contrast-enhanced CBCT and Contrast-enhanced CT for Abdominal Aortic Aneurysm Stenting", Medical Image Computing and Computer-Assisted Intervention, 2013, Springer Berlin Heidelberg, 9 pgs.
Brounstein et al., "Towards Real-Time 3D US to CT Bone Image Registration Using Phase and Curvature Feature Based GMM Matching", Medical Image Computing and Computer-Assisted Intervention, 2011, Springer Berlin Heidelberg, pp. 236-242.
Wu et al., "Scalable High Performance Image Registration Framework by Unsupervised Deep Feature Representations Learning" IEEE Transactions on Biomedical Engineering, Jul. 2016, vol. 63, No. 7, 32 pgs.
Fischer et al., "FlowNet: Learning Optical Flow with Convolutional Networks", IEEE Conference on Computer Vision, May 4, 2015, arXiv:1504.06852v2, 13 pgs.
Wohlhart et al., "Learning Descriptors for Object Recognition and 3D Pose Estimation", 2015 IEEE Conference on Computer Vision and Pattern Recognition, 10 pgs.
Parisotto et al., "Actor-Mimic: Deep Multitask and Transfer Reinforcement Learning", ICLR, Feb. 22, 2016, arXiv:1511.06342v4, pp. 1-16.
Simonyan et al., "Deep Inside Convolutional Networks: Visualising Image Classification Models and Saliency Maps", Dec. 20, 2013, arXiv:1312.6034v1, pp. 1-8.
Besl et al., "Method for Registration of 3-D Shapes", IEEE Transactions on Pattern Analysis and Machine Intelligence, vol. 14, No. 2, Feb. 1992, pp. 239-256.
Ibanez et al., The ITK Software Guide, Aug. 21, 2003, 565 pgs.
Sotiras et al., "Deformable Medical Image Registration: A Survey", IEEE Transactions on Medical Imaging, vol. 32, No. 7, Jul. 2013, 72 pgs.
Bronstein et al., "Data Fusion through Cross-modality Metric Learning using Similarity-Sensitive Hashing", Computer Vision and Pattern Recognition (CVPR), IEEE Conference, 2010, pp. 1-8.
Weinzaepfel et al., "DeepFlow: Large Displacement Optical Flow with Deep Matching", IEEE International Conference on Computer Vision, Dec. 2013, Sydney, Australia, 9 pgs.
Dosovitskiy et al., "FlowNet: Learning Optical Flow with Convolutional Networks", IEEE International Conference on Computer Vision, Dec. 2015, 9 pgs.
Kingma et al., "Semi-Supervised Learning with Deep Generative Models", Advances in Neural Information Processing Systems, arXiv:1406.5298v2, Oct. 31, 2014, pp. 1-9.
Long et al., "Fully Convolutional Networks for Semantic Segmentation", Mar. 8, 2015, Proceedings of the IEEE Conference on Computer Vision and Pattern Recognition, Mar. 8, 2015, arXiv:1411.4038v2, 10 pgs.
Chen et al., "3D Meshless Prostate Segmentation and Registration in Image Guided Radiotherapy", Medical Image Computing and Computer-Assisted Intervention, 2009, Springer-Verlag Berlin Heidelberg, pp. 43-50.
Lu et al., "A Pre-Operative CT and Non-Contrast-Enhanced C-arm CT Registration Framework for Trans-Catheter Aortic Valve Implantation", Computerized Medical Imaging and Graphics, vol. 38, Issue 8, Dec. 2014, pp. 683-695.
Neumann et al., "A Self-Taught Artificial Agent for Multi-Physics Computational Model Personalization", Medical Image Analysis, Apr. 21, 2016, vol. 34, pp. 52-64.
Hausknecht et al., "Deep Reinforcement Learning in Parameterized Action Space", CLR, 2016, pp. 1-12.
Caicedo et al., "Active Object Localization with Deep Reinforcement Learning", In Proceedings of the IEEE International Conference on Computer Vision, 2015, 9 pgs.
Silver et al., "Mastering the Game of Go with Deep Neural Networks and Tree Search", Nature, Jan. 28, 2016, vol. 529, 20 pgs.
Mnih et al., "Human-Level Control Through Deep Reinforcement Learning", Nature, Feb. 26, 2015, vol. 518, 13 pgs.
Rios et al., "Derivative-Free Optimization: A Review of Algorithms and Comparison of Software Implementations", Journal of Global Optimization, 2013, pp. 1247-1293.

(56) References Cited

OTHER PUBLICATIONS

Razlighi et al., "Evaluating Similarity Measures for Brain Image Registration", Journal of Visual Communication and Image Representation, Oct. 2013, vol. 24, No. 7, 29 pgs.
Murphy et al., "Evaluation of Registration Methods on Thoracic CT: The EMPIRE10 Challenge", IEEE Transactions on Medical Imaging, vol. 30, No. 11, Nov. 2011, pp. 1901-1920.
Markelj et al., "A Review of 3D/2D Registration Methods for Image-Guided Interventions", Medical Image Analysis, vol. 16, Apr. 2012, pp. 642-661.
Liao et al., "A Review of Recent Advances in Registration Techniques Applied to Minimally Invasive Therapy", IEEE Transactions on Multimedia, Aug. 2013, 18 pgs.
James et al., "Medical Image Fusion: A Survey of the State of the Art", Information Fusion, Sep. 2014, 45 pgs.
Oliveira et al., "Medical Image Registration: a Review", Computer Methods in Biomechanics and Biomedical Engineering, 2014, 49 pgs.
Neumann et al., "Probabilistic Sparse Matching for Robust 3D/3D Fusion in Minimally Invasive Surgery", IEEE Transactions on Medical Imaging, Jul. 29, 2014, vol. 34, Issue 1, Jan. 2015, pp. 49-60.
Miao et al., "A CNN Regression Approach for Real-Time 2D/3D Registration", IEEE Transactions on Medical Imaging, vol. 35, Issue 5, Feb. 2016, pp. 10-13.
Jaderberg et al., "Spatial Transformer Networks", Neural Information Processing Systems, 2015, pp. 1-9.
Lotfi et al., "Improving Probabilistic Image Registration via Reinforcement Learning and Uncertainty Evaluation"; Network and Parallel Computing, Springer International Publishing; Cham, Sep. 22, 2013, 9 pgs.
Hill et al. "Registration Methodology : Concepts and Algorithms" In: "Medical Image Registration", Jan. 2001, CRC Press, 27 pgs.
Harmon et al., "Reinforcement Learning: A Tutorial Scope of Tutorial", retrieved from the Internet on Oct. 27, 2016, Jan. 1, 1996, 17 pgs.
Chinese Office Action dated Mar. 23, 2020 in corresponding Chinese Patent Application No. 201710351955.5.
Partial Search Report dated Dec. 1, 2017 in corresponding European patent application No. 17171689.7.
Chinese Office Action dated Sep. 24, 2021 in corresponding Chinese Patent Application No. 201710351955.5.
Thévenaz, Philippe et al: "Optimatiozation of Mutual Information for Multiresolution Image Registration"; IEEE Transactions on Image Processing; vol. 9, No. 12, pp. 2083-2099.
Hong, Lan et al: "Medical Image Registration Algorithm based on Optimising Mutual Information and CNN with Particle Swarm"; Computer Applications and Software; vol. 32, No. 12, pp. 201-205, Year: Dec. 2015.

* cited by examiner

METHOD AND SYSTEM FOR IMAGE REGISTRATION USING AN INTELLIGENT ARTIFICIAL AGENT

CROSS-REFERENCE TO RELATED APPLICATIONS

This application is a continuation of U.S. patent application Ser. No. 15/587,094, filed May 4, 2017, which claims the benefit of U.S. Provisional Application No. 62/338,059, filed May 18, 2016, U.S. Provisional Application No. 62/344,125, filed Jun. 1, 2016, and U.S. Provisional Application No. 62/401,977, filed Sep. 30, 2016, the disclosures of which are herein incorporated by reference in their entirety.

BACKGROUND OF THE INVENTION

The present invention relates to registration of medical images, and more particularly to computer-based automated medical image registration using an intelligent artificial agent.

Medical image registration is an important technology that enables image guided therapy, automated diagnosis imaging, and machine-driven image understanding. The goal of image registration is to recover correspondences between two or more medical images, which can be acquired from different patients/objects, the same patient at different time points, different medical imaging modalities, etc., in order to align or fuse the images. The aligned images can provide important information in various applications. For example, the aligned images can be used to guide minimally invasive therapy by fusing pre-operative volume scans (e.g., MRI) with interventional imaging (e.g., DynaCT or fluoroscopy), or to provide complimentary diagnostic information (e.g., co-registration of cardiac ultrasound and MRI for joint function, flow and substrate analysis) or longitudinal analysis (e.g., radiotherapy monitoring through longitudinal CT scans). Due to the vast range of applications to which image registration can be applied, it is challenging to develop a general image registration method that works robustly for all uses.

Image registration problems are typically treated as optimization problems in which a generic matching metric (e.g., Mutual Information, Cross Correlation, etc.) is defined to measure the similarity of image pairs to be registered, and transformation parameters between the two images (e.g., rigid body, affine, deformable) are then estimated by an optimizer (e.g., Simplex, Powell, trust region optimization, etc.) via maximization of the defined matching metric. To work robustly, such optimization-based image registration methods typically require extensive hand-crafted engineering for individual registration tasks by incorporating prior knowledge about the specific anatomies, imaging modalities and expected artifacts, or workflows at hand. One reason for this is that a generic matching metric does not guarantee a good representation of the accuracy of the alignment of the data at hand for all use cases, in all circumstances. That is, the global maximum of the matching metric does not necessarily correspond to the correct alignment of the images, for example when the data is noisy, partially occluded, or with drastic different appearances due to different imaging physics. Therefore, the hand-crafted engineering of the matching metric is often required for the specific registration task, for example, by introducing a task-specific region-of-interest (ROI) or calculating hand-crafted features. In addition, a generic matching metric is often non-convex for a given registration task and generic optimizers typically perform poorly on non-convex optimization problems. To avoid being trapped into local minima, prior knowledge is often incorporated to develop optimization schemes for specific registration tasks, for example by prior knowledge-driven initialization/seeding, hierarchical optimization or application specific regularizers.

BRIEF SUMMARY OF THE INVENTION

The present invention provides methods and systems for registration of medical images using an intelligent artificial agent. Embodiments of the present invention provide artificial intelligent agents that learn registration tasks from training data, and achieve better and better registration results as more data are used for training.

In one embodiment of the present invention, a current state observation of an artificial agent is determined based on a plurality of medical images and current transformation parameters. Action-values are calculated for a plurality of actions available to the artificial agent based on the current state observation using a machine learning based model trained based on a plurality of registered training images, wherein the plurality of actions correspond to predetermined adjustments of the transformation parameters. An action having a highest action-value is selected from the plurality of actions and the transformation parameters are adjusted by the predetermined adjustment corresponding to the selected action. The determining, calculating, and selecting steps are repeated for a plurality of iterations, and the plurality of medical images are registered using final transformation parameters resulting from the plurality of iterations.

The machine learning based model used to calculate the action-values based on the current state observation may be a trained deep neural network (DNN). The trained DNN may be trained to predict action-values for the plurality of actions based on a plurality of training image pairs with known ground truth transformation parameters using reinforcement learning in which, for each training image pair, a reward for each action of the plurality of actions at a given state is used to train the DNN to learn an optimal registration policy. The trained DNN may be trained using supervised reinforcement learning, in which the reward for each action of the plurality of actions at a given state is directly calculated based on a decrease in a geodesic distance between the transformation parameters at the given a state and the ground truth transformation parameters for the training image pair resulting from applying the action. The plurality of training image pairs may include training image pairs synthetically generated by artificially de-aligning other training image pairs using randomly generated perturbations to the ground truth transformation parameters of the other training image pairs. The plurality of training image pairs may include training image pairs synthetically generated from other training image pairs to provide dense sampling close to the ground truth transformation parameters by co-deforming the other training image pairs by randomly generated affine transformations within a range of the ground truth transformation parameters. The plurality of training image pairs includes training image pairs synthetically generated by artificially altering image appearance of other training image pairs using synthetic image generators.

In an embodiment, the transformation may be a rigid-body transformation and the plurality of actions may comprise actions corresponding to predetermined adjustments of translation and rotation rigid-body transformation parameters. The plurality of actions may comprise respective actions corresponding to increasing and decreasing each of the translation and rotation rigid-body parameters by a constant or time-varying step size. The rigid-body transformation may be a 3D rigid-body transformation with rigid-body transformation parameters including three translation parameters and three rotation parameters. The rigid-body transformation may be a 2D rigid-body transformation with rigid-body transformation parameters including two translation parameters and one rotation parameter.

In an embodiment, wherein the plurality of medical images may include a first medical image and a second medical image and the transformation may be a dense deformation model that models deformations applied to the second medical image. The plurality of actions may comprise actions corresponding to adjustments to parameters of the deformation model. The first and second medical images may be registered by generating a dense deformation field corresponding to final parameters of the deformation model resulting from the plurality of iterations and warping the second medical image to register the second medical image with the first medical image by applying the dense deformation field corresponding to the final parameters of the deformation model.

In an embodiment, the intelligent artificial agent based image registration may be performed hierarchically using multi-scale image data. The determination of the current state observation, calculation of the action-values, and selection of the action having the highest action value may be repeated using a first image resolution of the plurality of medical images and a first machine learning based model trained using training images at the first image resolution until a first stop condition is reached. The determination of the current state observation, calculation of the action-values, and selection of the action having the highest action value may then be repeated using a second image resolution of the plurality of medical images and a second machine learning based model trained using training images at the second image resolution until a second stop condition is reached.

In another embodiment, a method for training an intelligent artificial agent to perform image registration according may include obtaining training image pairs and generating synthetic training image pairs, defining a state observation input for the artificial agent, defining a set of possible actions available to the artificial agent, defining a reward mechanism for learning a registration policy, and training a deep neural network (DNN) to predict action-values for the set of possible actions based on the state observation input using the training image pairs.

These and other advantages of the invention will be apparent to those of ordinary skill in the art by reference to the following detailed description and the accompanying drawings.

DETAILED DESCRIPTION

The present invention relates to registration of medical images using an intelligent artificial agent. Embodiments of the present invention are described herein to give a visual understanding of the image registration methods. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system or available through a network system.

Image registration refers to the alignment of two or more images or transformation of different images into one coordinate system. For example, medical image registration can be used to recover correspondences between two or more images acquired using from different patients, the same patient at different times, different medical imaging modalities (e.g., computed tomography (CT), magnetic resonance imaging (MRI), positron emission tomography (PET), ultrasound, etc.), and/or statistical or geometric models. The images can be brought into the same coordinate system via various transformation models, such as, but not limited to, rigid-body transformation, affine transformation, parametric splines, and dense motion fields. Medical image registration is utilized in many different applications. For example, the aligned images can provide complimentary information for fusion-based decision making (e.g., cardiac assessment from MR, CT and ultrasound), motion compensation in image reconstruction (e.g., to cope with breathing motion), enabling longitudinal change analysis (e.g., follow-up reading of cancer patients by registering new and past images of the same patient), or guiding minimally invasive therapy (e.g., fusion of preoperative medical image data into the surgical coordinate system for guidance).

Figure 1A:
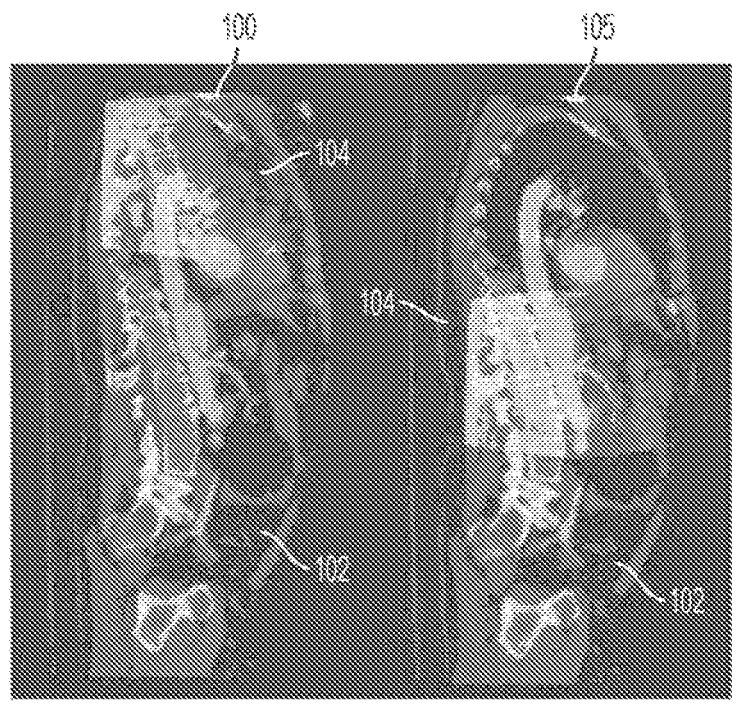
FIGS. 1A and 1B illustrate examples of medical image registration problems that present challenges to traditional optimization based image registration techniques.
Figure 1B:
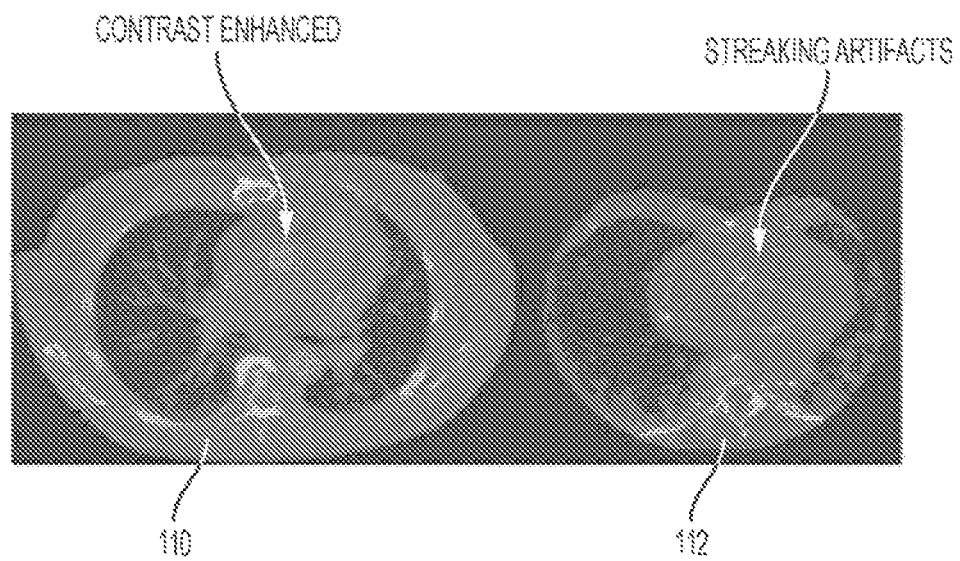

In the following, embodiments of the present invention will be described using the pair-wise image registration case. However, the embodiments described herein can easily be extended to the case of group-based registration, where a group of images are all registered to the same reference image (e.g., one of the images in the group or an atlas image) simultaneously. Image registration has typically been formulated as an optimization problem, where a generic matching metric is defined to measure the similarity of the image pairs to be registered. The transformation parameters between the image pairs are then estimated via maximization of a pre-defined matching metric using an optimizer. This formulation faces significant challenges in registering medical images. FIGS. 1A and 1B illustrate examples of medical image registration problems that present challenges to traditional optimization based image registration techniques. One challenge of traditional optimization based image registration is that a generic matching metric is often non-convex for medical images, and generic optimizers typically perform poorly on non-convex problems. This may be an issue in cases in which there is a large difference in the field of view (FOV) of the images to be registered, such as example shown in FIG. 1A. FIG. 1A shows an overlay of a spine CT volume 102 and a Conebeam CT (CBCT) volume 104 before registration (100) and after registration (105), with a large difference in FOV between the CT and CBCT volumes 102 and 104. The large difference in the FOV between the CT and CBCT volumes 102 and 104 to be registered can result an optimizer finding a number of local maximums of the matching metric due to the repetitive nature of the vertebra. Another challenge of traditional optimization based image registration is that a generic matching metric is often sensitive to image noise and artifacts, such as in the example of FIG. 1B, to partial coverage of the organ of interest (due to field of view or prior surgery for instance), and to drastically different appearances due to different imaging physics (e.g. ultrasound/MRI registration for cardiac image fusion). FIG. 1B shows a cardiac CT volume 110 with contrast enhanced vessels and a cardiac CBCT volume 112 with soft tissue contrast and streaking artifacts. This use case of registering cardiac CT and cardiac CBCT is very common for cardiac interventions, and is often used in a catheterization laboratory (cath lab) to fuse preoperative information to interventional images for guidance of valve replacement, PCI, and other interventions. In FIG. 1B, the differences in the CT and CBCT volumes 110 and 112 due to the streaking artifacts and the difference in appearance of the vessels may result in an inaccurate registration of the CT and CBCT volumes 110 and 112 using traditional optimization based image registration.

Embodiments of the present invention reformulate medical image registrations problems by training an intelligent artificial agent to more closely mimic how humans perform image registration as a process of sequential actions of object recognition and manipulation. Embodiments of the present invention train an intelligent artificial agent to register image pairs through a combination of supervised learning and hierarchical image processing. The embodiments can be extended to the registration of groups of images by different strategies, such as extending the number of actions so that there is a set of actions for each image or by running a set of agents together, at the same time and cooperatively. The intelligent artificial agent is implemented on one or more computers or processors by executing computer program instructions (code) loaded into memory. The intelligent artificial agent observes its environment (i.e., the images to be registered) and autonomously acts on that environment to register the images using a registration strategy (herein referred to as a "policy" to be consistent with reinforcement learning terminology) learned using machine learning. The agent can be triggered on demand, or be persistent and always running in the background, ensuring robust image registration even if one of the image moves, for instance due to patient motion in the case of real-time imaging. The input for the intelligent artificial agent (the fixed image and the updated moving image as it is transformed by the current estimate of the transformation parameters) is used to determine its "state", which corresponds to the current alignment of the raw image pairs. The output of the intelligent artificial agent is an "action" to improve the alignment between the fixed and moving image by changing the parameters that define the transformation between the images. In an advantageous embodiment of the present invention, a deep neural network (DNN) is used to approximate the state-value function which returns for each state, a value for each possible action which indicates how good that action is. Other approximation functions can be used in alternative embodiments. During training, the intelligent artificial agent learns a registration policy via a DNN that maps the current state to the optimal action that best improves the accuracy of the alignment. During testing, in order to register newly input images, the trained artificial agent applies the learned registration policy to improve the alignment of the images until it converges to the correct pose. By using this deep learning model, embodiments of the present invention are advantageous in that the intelligent artificial agent can inherently learn both a data-driven matching metric and a task-driven policy from raw image data without hand-crafted engineering and perform robust medical image registration.

Figure 2:
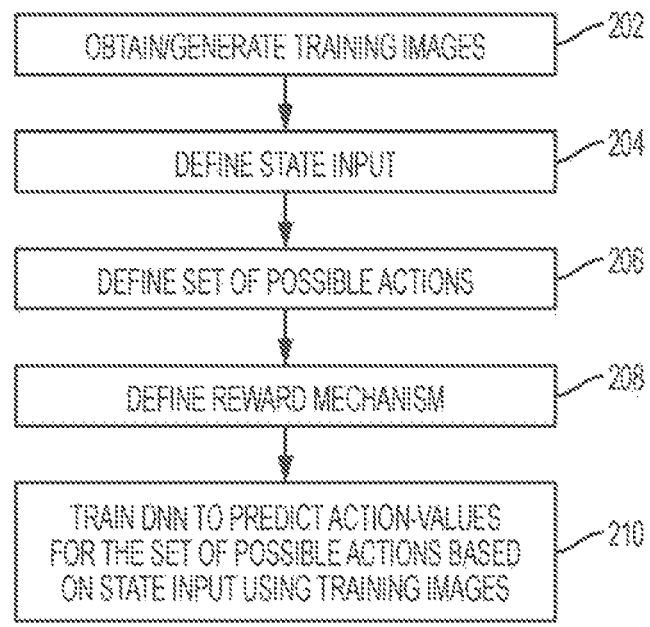
FIG. 2 illustrates a method for training an intelligent artificial agent to perform image registration according to an embodiment of the present invention.

FIG. 2 illustrates a method for training an intelligent artificial agent to perform image registration according to an embodiment of the present invention. When registering a pair of images, one image is designated as the reference image or fixed image and the other image is designated as the moving image or floating image. The reference and moving images to be registered can be denoted as $I_{ref}:R^N \rightarrow R$ and $I_{mov}:R^M \to R$, respectively, where N and M are the respective dimensionalities of the two images to be registered. In medical images N and M are typically equal to 2, 3, or 4 (3D+time). For example, in 3D/3D registration, N=M=3. In 2D/2D registration, N=M=2. In 2D/3D, N=2 and M=3. Time series could be registered globally as well. In this case, N=M=4. The goal of image registration is to estimate a transformation, denoted as $T:R^N \to R^M$, that transforms the moving image $I_{mov}$ to be aligned with the reference image $I_{ref}$. The transformation, in general terms, can represent a curved manifold and can be modeled using K transformation parameters. The goal of the registration then becomes estimating the K transformation parameters such that the similarity between $I_{ref}$ and $I_{mov}$ is maximized. In some embodiment, various types of transformation models, such as an affine transformation, spline model, or biomechanical model, can be used to model the transformation of the moving image $I_{mov}$ to be aligned with the reference image $I_{ref}$. In other embodiments, a non-parametric deformable registration can be estimated with a dense motion field. In this case, motion parameters can be estimated for each pixel/voxel on the grid, and the motion parameters can be the displacement directly, stationary velocities, or kinetic moments, or any subspace representation of those (e.g., PCA modes among others). The method of FIG. 2 trains a deep neural network (DNN) to predict action-values for a set of actions corresponding to the transformation parameters. By parameterizing the action space, the DNN can be trained to perform any registration task using the method of FIG. 2.

Referring to FIG. 2, at step 202, training images are obtained and/or generated. In an advantageous embodiment, the DNN can be trained for a particular registration task based on training image pairs (i.e., a reference image $I_{ref}$ and a moving image $I_{mov}$) corresponding to the particular registration task and known ground truth transformations between the training image pairs. For example, the training image pairs may be medical images acquired using different imaging modalities (e.g., CT, MRI, ultrasound, PET, etc.), medical images acquired from the same patient (using the same imaging modality) at different times, or medical images acquired from different patients. The training image pairs can be pairs of 3D medical images for 3D/3D registration, pairs of 2D medical images for 2D/2D registration, or a 3D image and a 2D image for 2D/3D registration. The training image pairs can include actual medical images of patients acquired from medical image acquisition devices, such as a CT scanner, MRI scanner, C-arm image acquisition device, ultrasound device, etc. These training image pairs can be obtained by receiving the images from the image acquisition devices used to acquire the images or by loading previously acquired images from a storage or memory of a computer system. The ground truth transformation for these image pairs can be acquired by manual expert annotation or by applying an existing image registration method. In cases in which an existing registration method is used to compute the ground truth transformation for a training image pair, the reference image in the training image pair may be replaced with the transformed moving image using the computed transformation resulting from the existing registration method, in order to compensate for inaccuracies in the existing registration method.

The training image pairs can also include synthetic images which are generated by augmenting other training images rather than being acquired in a scan of a patient using an image acquisition device. It may be difficult to obtain a large number of labeled training pairs of actual scanned medical images of patients. According to an advantageous embodiment, a large training set can be synthetically generated from a small number of labeled training pairs. In order to generate synthetic training image pairs, each of the aligned training image pairs with a known ground truth transformation can be artificially de-aligned by transforming one of the images with a set of transformations sampled in the space of the transformation parameters. Since the original ground truth transformation is known, each of these transformation results in an additional training image pair for which the ground transformation is also known. In addition, in order to provide denser sampling of the transformation parameter space close to the ground truth transformation, each aligned training image pair can be co-deformed by a number of perturbations within specified range of the ground truth transformation parameters to generate additional training image pairs that are close to the ground truth transformation in the transformation parameter space. Additional synthetic training images may also be generated by altering the appearance of one or both images in existing training pairs by adding noise and/or artifacts, or even by simulating other imaging modalities from unpaired training images using synthetic image generators including, but not limited to, physics-based simulators (e.g., MRI simulator, ultrasound simulator) or machine learning based simulators (e.g., training a generative adversarial network (GAN) to simulate an imaging modality from another one, the GAN being trained on paired images).

At step 204, the state input to the DNN is defined for the particular image registration task for which the DNN is being trained. The state that is input to the DNN is an observation of the current alignment of the two images. Given two images $I_{ref}$ and $I_{mov}$ to be registered and current and previous transformation parameters $\{m_t\}_{t=-\tau, \ldots, 0}$, the intelligent artificial agent extracts an observed state of the current alignment, and inputs the state to the DNN. The state observation can include the current and previous transformation parameters $\{m_t\}_{t=-\tau, \ldots, 0}$; the whole image or a region of interest (ROI) of the reference image $I_{ref}$; the whole image or ROIs of the moving image $I_{mov}$ transformed by the transformations specified by $\{m_t\}_{t=-\tau, \ldots, 0}$; the whole image or ROIs of J transformed by transformations derived from $\{m_t\}_{t=-\tau, \ldots, 0}$, e.g., via perturbation; in the case of 2D/3D registration (N=2, M=3), the whole image or ROIs of 2D projections of $I_{mov}$ transformed by the transformation specified by $\{m_t\}_{t=-\tau, \ldots, 0}$; in the case of 2D/3D registration (N=2, M=3), the whole image or ROIs of 3D projections of $I_{mov}$ transformed by transformations derived from $\{m_t\}_{t=-\tau, \ldots, 0}$, e.g., via perturbation; and/or the above images post-processed by operations such as filtering, subtraction, etc. In one embodiment, the state of the current alignment can be computed by comparing the transformed moving image $I_{mov}$ using current transformation parameters (or projections of the transformed moving image in the case of 2D/3D registration) and the reference image $I_{ref}$ using a specified function or operation. For example, in an advantageous implementation, the state of the current alignment can be computed by subtracting the transformed moving image $I_{mov}$ using current transformation parameters from the reference image $I_{ref}$. In another embodiment, the reference image $I_{ref}$ and the transformed moving image $I_{mov}$ using current transformation parameters are passed to the neural network which features a multi-channel architecture (for example, in FIG. 12). The comparison of the images is then automatically performed and learned by the neural network.

At step 206, a set of possible actions are defined for the registration task. The set of possible actions include a set of actions that alter the transformation parameters. For example, to perform rigid registration, the set of actions can include actions that alter rigid body transformation parameters (e.g., 3 translation parameters and 3 orientation parameters for 3D/3D registration). For deformable registration, a deformation model can be used to model the deformation field and the set of actions can include actions that alter parameters of the deformation model used to model the deformation field. The set of possible actions can include actions to change (increase and decrease) individual transformation parameters by a certain step size $\delta$, actions to change multiple (l) transformation parameters simultaneously by certain step sizes $\delta_1 \ldots \delta_l$, actions to optimize the step size $\delta_i$ (i=1 ... k) for each transformation parameter, an action that determines that the correct registration is achieved and terminates the registration process, and an action that compounds the transformation resulting from the previously selected actions in the curved manifold of registration parameters to ensure that the entire path of corrective actions stay within the manifold. It is to be understood that the present invention is not limited to the above described actions and other actions may be included based on the particular registration task for which the intelligent artificial agent is trained.

At step 208, a reward mechanism is defined. A reward mechanism is defined that assigns a reward for each action, depending on the effect of that action of the resulting alignment of the images. A higher reward is assigned for actions that lead to more accurate alignment, while a lower reward or penalty (negative reward) is assigned for actions that lead to less accurate alignment. Reinforcement learning can then be used to train the agent. In an advantageous embodiment, the reward mechanism can be defined as the reduction of L2 error in the transformation parameters:

$$\text{reward} = \|m_{after} - m_{gt}\|_2 - \|m_{before} - m_{gt}\|_2 \quad (1)$$

where $m_{before}$ and $m_{after}$ are the transformation parameters before and after taking the action, and $m_{gt}$ is the ground truth parameters for the correct registration. In this case, the agent training is fully supervised and this type of reward can be thought of as a "GPS", which directly tells the agent what is the best action to take. After performing several trials and learning from the "GPS" (training phase), one can turn off the "GPS" (testing phase) and the registration strategy learned from the "GPS" in the training phase can be applied to register images for which the transformation is not yet known.

At step 210, a DNN is trained to predict action-values for the set of possible actions based on the state input using the training images. A core part of the intelligent agent is a DNN (or possibly multiple DNNs) that takes the state as input and outputs action-values for all possible actions with proper parametrization for the particular image registration task. The action-value for an action can represent the highest possible future reward if an action is taken discounted based on the number of steps to reach the ground truth transformation parameters. With the reward mechanism described above (e.g., reduction of L2 error in the transformation parameters), a higher action-value indicates that the action is driving the registration toward the correct direction (i.e., toward the correct final registration result) and therefore is the preferred action to be taken. The action space can be discrete or continuous with parameterization.

According to an advantageous embodiment of the present invention, the DNN can be trained using a supervised Deep Reinforcement Learning (DRL) technique. Reinforcement Learning (RL) is a type of machine learning in which a software based artificial agent uses reward feedback to automatically learn ideal behavior in a specific context and for a specific task. In DRL, which combines DNNs with RL and has recently been applied to train an artificial agent to play Atari and Go games, a policy learning process is formulated as a RL problem and the action-value function (also known as Q function) is estimated following the Bellman equation as an iterative update. In DRL and RL, the training of the agent is typically unguided and the agent is free to evolve in its environment according to its current policy estimate. However, training efficiency of the agent and iterative update of the Q function is relatively low, which could render DRL impractical or impossible for image registration tasks where the input data and the parameter space is large, such as registration of 3D medical image volumes. In an advantageous embodiment of the present invention the DRL training of the DNN is supervised based on the known ground truth transformations of the training image pairs using a greedy search strategy in which the action-values are approximated analytically. This supervised DRL has an advantage that the Q-network guarantees to converge and the behavior distribution can be arbitrarily smooth without the need to deploy a memory replay strategy, which can have a very high memory footprint. The DNN can be trained in an end-to-end fashion, or can be trained separately for image feature extraction layers and policy learning layers in order to bring more robustness to variations in image content if needed.

In an alternative embodiment, the trained DNN can be trained to predict the action-values based on the training image pairs using evolution strategies (ES) to learn the parameters (e.g., weights) of the DNN. In ES, instead of using reinforcement learning, genetic-like algorithms or sampling strategies are used to optimize the parameters of the DNN directly based on the training data.

The trained DNN is stored, for example, in memory or storage of a computer system or on a remote "cloud-based" computer system. The trained DNN can then be loaded and used when registering two newly received images to iteratively predict action-values for each of the set of possible actions based on the current state of the images to be registered and execute the selected action having the highest predicted action-value.

Figure 3:
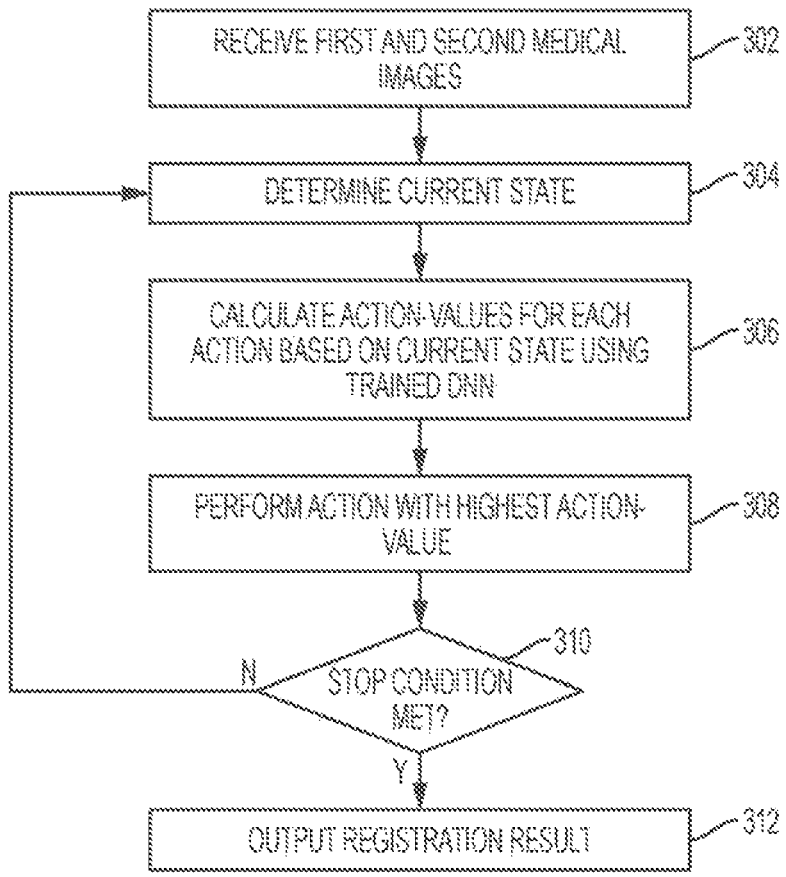
FIG. 3 illustrates a method for image registration using an intelligent artificial agent according to an embodiment of the present invention.

FIG. 3 illustrates a method for image registration using an intelligent artificial agent according to an embodiment of the present invention. At step 302, first and second medical images are received. For example, the first and second medical images can be images acquired using different imaging modalities (e.g., CT, MRI, ultrasound, PET, DynaCT, etc.), images of the same patient acquired at different times, or images acquired from different patients. The first and second medical images may both be 3D medical images (volumes) (3D/3D registration), both be 2D medical images (2D/2D registration), or may be one 2D medical image and one 3D medical image (2D/3D registration). The first sand second medical images may also be image sequences (3D+t or 2D+t), which can also be registered using the method of FIG. 3. The first and second medical images may be received directly from image acquisition devices, such as a CT scanner, MRI scanner, ultrasound device, C-arm image acquisition device, etc., or may be received by loading previously stored medical images from a memory or storage of a computer system or receiving the medical images in an electronic transmission from another computer system. One of the medical images is designated as the reference image $I_{ref}$ and the other is designated as the moving image $I_{mov}$.

At step 304, the current state is determined based on the first and second medical images and the current set of transformation parameters. At step 306, the current state is input to the trained deep neural network and action-values for the set of possible actions are calculated based on the current state using the trained DNN. The possible actions can correspond to adjustments to the transformation parameters. At step 308, the action with the highest action-value is selected and performed. The selected action will typically adjust at least one transformation parameter, which changes the transformation of the moving image $I_{mov}$. At step 310, it is determined if a stop condition has been met. For example, the stop condition can be reached if it is determined that a correct registration is achieved or when a maximum number of iterations have been performed. It can be determined that a correct registration is achieved when a "stop registration" action is selected as the action with the highest action-score or by comparing an error value between the reference image and the transformed moving image to a predetermined threshold value. If the stop condition is not met, the method returns to step 304 and repeats steps 304-310. Accordingly, steps 304-310 are iterated until the stop condition is met. When the stop condition is met, the method proceeds to step 312. At step 312, the registration result is output. The moving image is transformed by the final transformation parameters, and the transformed moving image and the reference image can be displayed on a display of a computer system. For example, the transformed moving image can be overlaid on the reference image and be displayed as a fused image. The registered images can also be electronically transmitted to a remote computer system to be displayed on a display of the remote computer system. Although FIG. 3 only shows outputting the final registration result, it is also possible that the incremental registration results using the current transformation parameters can be output (e.g., displayed on a display of a computer system) as each iteration of steps 304-310 is performed. Such incremental results would allow a user to view each adjustment made by the intelligent artificial agent in real-time as the artificial agent is registering the images.

Figure 4:
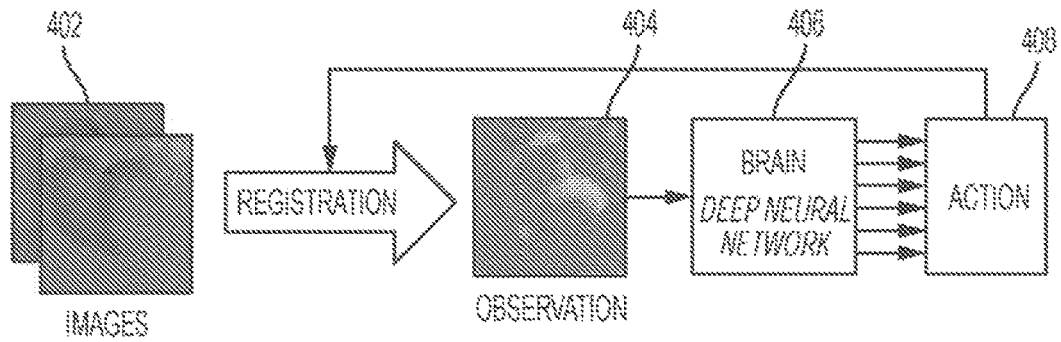
FIG. 4 illustrates a framework for artificial agent image registration using the method of FIG. 3 according to an embodiment of the present invention.

FIG. 4 illustrates a framework for artificial agent image registration using the method of FIG. 3 according to an embodiment of the present invention. As shown in FIG. 4, two medical images 402 to be registered are received. The state 404, which is an observation of the current alignment of the images 402, is determined based on the current transformation parameters. For example the state observation 404 can be an image resulting from subtracting the moving image as transformed by the current transformation parameters from the reference image. The state observation 404 is input to the trained DNN 406, which acts as the "brain" of the intelligent artificial agent. The trained DNN 406 calculates a respective action-score for each action in a set of possible actions, and the action 408 with the highest action score is selected. The action 408 is performed to adjust at least one of the transformation parameters, and registration is performed with the updated transformation parameters, resulting in an updated state observation 404. This process is iterated until a stop condition is met. For example, the process can be iterated until a stop registration action is selected or until a predetermined maximum number of iterations are performed.

In a possible embodiment, multiple agents can be trained in a coordinated fashion to register multiple objects (e.g., organs, anatomical structures, etc.) in the images simultaneously. In one exemplary implementation, each object is aligned independently in each step by a corresponding agent (with a corresponding DNN) trained to register that object, and a master agent is trained to coordinate the actions suggest from the individual object-specific agents and output the optimal overall action given the constraints of the relative positions of the multiple objects to be registered. In another possible implementation, each agent can be trained to collaborate with other agents and/or unknown teammates. Similarly, multiple agents can also be trained in a coordinated fashion to register multiple images simultaneously by incorporating the constraints of the relative transformations among the images.

In another possible embodiment, a multi-task agent can be trained to perform registration of a variety of images coming from different sources, e.g., varying modalities, imaging protocols, and organs. Transfer and hierarchical reinforcement learning can be applied to train the multi-task agent by transferring the knowledge from agents trained for individual registration tasks (e.g., specific organs) and abstracting the features and policies for registration. New task-specific agents can also be trained more efficiently by transferring the knowledge from previously trained agents on similar registration tasks. In this context, in an advantageous implementation, an actor-mimic approach can be used to train a single intelligent artificial agent capable of registering multiple different types of image pairs. Let N be the number of registration tasks, between N number of imaging modality pairs. N different artificial agents $A_i$ ($i \in 1 \ldots N$) can be trained as described above, each corresponding to a specific registration task between a specific type of imaging modality pairs. A "mimic" agent $A_m$ is then trained whose objective is to be as accurate and robust as all of the artificial agents $A_i$ in their respective tasks. In one embodiment, $A_m$ is trained using N different types of training image pairs and the loss function to minimize is the sum of the least-square differences between the action-values of $A_m$ and those of the respective individual agents $A_i$. Other loss functions can be designed to enable domain transfer and task generalization. With such a framework, the mimic agent will learn generic features present in all imaging modalities that will enable the registration task.

In another possible embodiment, an intelligent artificial agent can be trained to register the medical images in a coarse-to-fine manner using different transformation models. For example, the intelligent artificial agent may first adjust rigid-body transformation parameters until a first stop condition is reached (e.g., a predetermined number of iterations or a switch transformation model action is selected), then affine transformation parameters until a second stop condition is reached (e.g., a predetermined number of iterations or a switch transformation model action is selected), then polyaffine transformation parameters until a third stop condition is reached (e.g., a predetermined number of iterations or a switch transformation model action is selected), and then dense deformation parameters until a final stop condition is reached (e.g., a predetermined number of iterations or a stop registration action is selected). In this case, the trained DNN can be trained to calculate the action-values for actions corresponding to adjustments to all of the various transformation models (e.g., rigid, affine, polyaffine, dense) as well as action-values for actions corresponding switching between the various transformation models.

Rigid Registration Using an Intelligent Artificial Agent

In an advantageous embodiment of the present invention, an intelligent artificial agent is used to perform rigid registration of medical images. The rigid registration is described herein for 3D/3D medical image registration. It is to be understood that the methods for rigid registration described herein are not limited to t 3D/3D medical image registration and can be similarly applied to 2D/2D medical image registration as well. The methods for rigid registration described herein register images using a rigid-body transformation including three translation parameters and three rotation parameters. Such methods can be similarly applied to perform registration using other types of parametric transformations, such as a nine parameter affine transformation (three translation parameters, three rotation parameters, and three scale parameters), a 12 parameter affine transformation (three translation parameters, three rotation parameters, three scale parameters, and three shear parameters), or a poly-affine transformation.

Figure 5:
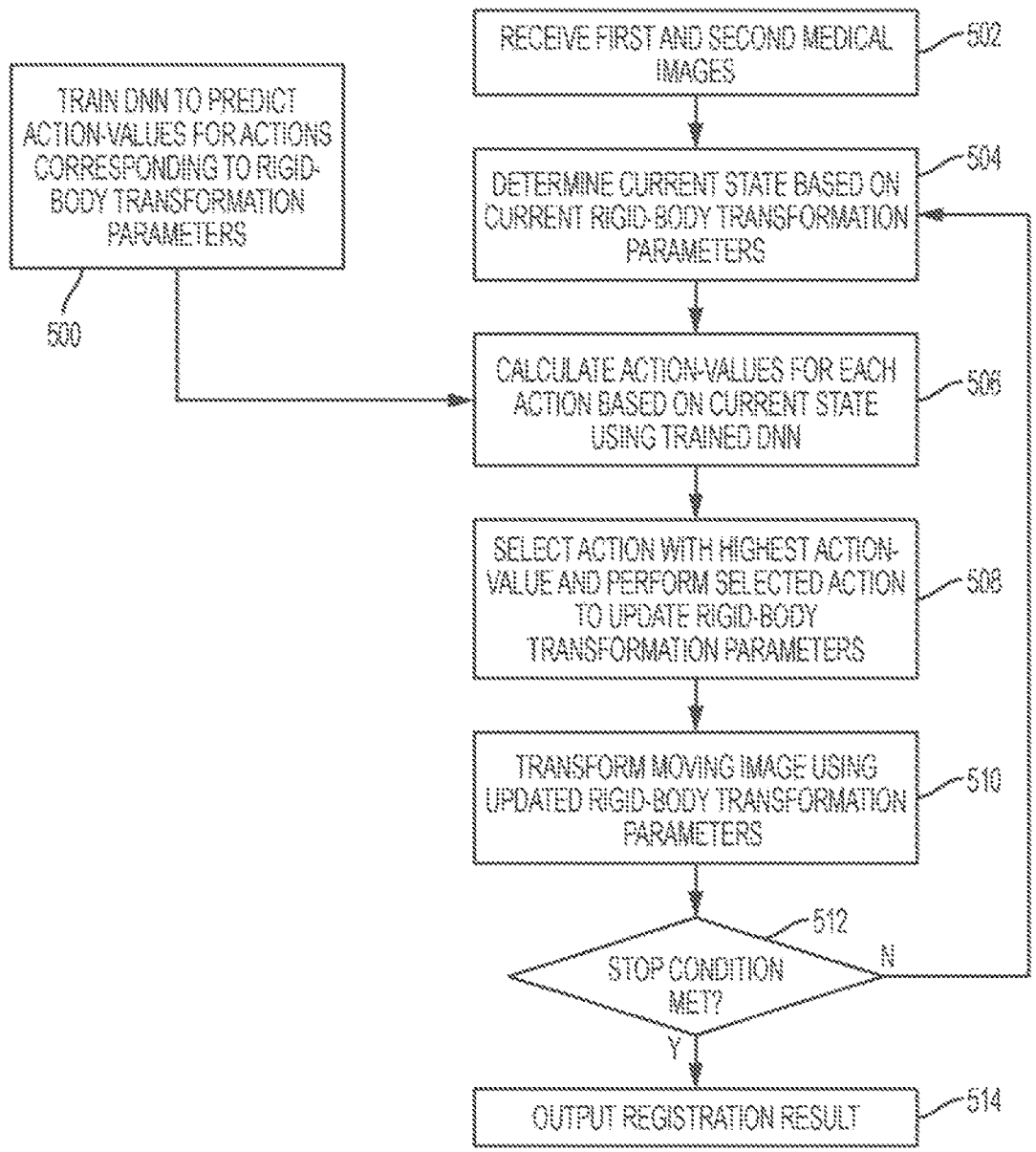
FIG. 5 illustrates a method for rigid registration of medical images using an intelligent artificial agent according to an embodiment of the present invention.

FIG. 5 illustrates a method for rigid registration of medical images using an intelligent artificial agent according to an embodiment of the present invention. At step 500 of FIG. 5, a DNN is trained to predict action-values for a set of actions corresponding to rigid-body transformation parameters. Step 500 is performed in an offline training stage prior to the on-line image registration for newly input/received images performed in steps 502-514.

Given a reference image $I_{ref}$ and a moving (floating) image $I_{mov}$, the goal of 3D/3D rigid-body image registration is to transform $I_{mov}$ using rigid-body transformation parameters m=$[t_x, t_y, t_z, \theta_x, \theta_y, \theta_z]$, represented by a column-wise homogenous transformation matrix as:

$$T_m = \begin{bmatrix} 1 & 0 & 0 & t_x \\ 0 & \cos\theta_x & -\sin\theta_x & t_y \\ 0 & \sin\theta_x & \cos\theta_x & t_z \\ 0 & 0 & 0 & 1 \end{bmatrix} \times \qquad (2)$$

$$\begin{bmatrix} \cos\theta_y & 0 & \sin\theta_y & 0 \\ 0 & 0 & 0 & 0 \\ -\sin\theta_y & 0 & \cos\theta_y & 0 \\ 0 & 0 & 0 & 1 \end{bmatrix} \times \begin{bmatrix} \cos\theta_z & -\sin\theta_z & 0 & 0 \\ \sin\theta_z & \cos\theta_z & 0 & 0 \\ 0 & 0 & 1 & 0 \\ 0 & 0 & 0 & 1 \end{bmatrix}$$

so that $I_{ref}$ and $I_{mov}$ are anatomically aligned. Here, a point in $I_{mov}$, represented in homogenous coordinates as $\vec{p}=[x, y, z, 1]^T$, is transformed to location $T_m\vec{p}$ in $I_{mov}(T_m)$. The problem can be cast as a Markov Decision Process (MDP), and the goal is to train an intelligent artificial agent that learns the policy to register two images by making a series of decisions based on the observation (state) of the current alignment. In an advantageous implementation, the current observation, or state $s_t$, is the intensity difference between $I_{ref}$ and $I_{mov}$ transformed using the current transformation parameters $m_t$:

$$s_t = I_{ref} - I_{mov}(T_{m_t}). \qquad (3)$$

In an advantageous implementation, the decision, or action $a_t$ is a change in one of the six transformation parameters (three translation parameters $t_x, t_y, t_z$ and three orientation parameters $\theta_x, \theta_y, \theta_z$) in $m_t$, e.g., $a_t$=[1, 0, 0, 0, 0, 0] for translation along the x-axis by 1 mm and $a_t$=[0, 0, 0, 1, 0, 0] for rotation around the x-axis by 1°. The next state $s_{t+1}$ is calculated via updating the moving image $I_{mov}$ by applying the action $a_t$:

$$m_{t+1} = m_t + a_t,$$

$$s_{t+1} = I_{ref} - I_{mov}(T_{m_{t+1}}). \qquad (4)$$

During training (step 500 of FIG. 5), the agent learns a registration policy using a DNN that maps the current state $s_t$ to the optimal action $a_{t,o}$. During testing (steps 502-514 of FIG. 5), the agent applies the learned policy in a sequence of N actions $\{a_{1,o}, \ldots, a_{N,o}\}$, to improve the alignment until it converges to the correct pose or a maximum number of iterations is reached.

The DNN can be trained using reinforcement learning. In an advantageous embodiment of the present invention, supervised DRL is used for training the DNN to predict action-values for the set of actions. The core problem is to find a policy that guides the decision process of the artificial agent. In previous DRL gaming applications, the policy learning is formulated as a RL problem with the action-value (also known as Q) function estimated following the Bellman equation as an iterative update. However, when relying on unguided explorations of the agent and iterative update of Q, training efficiency is relatively low. Indeed, this iterative update of Q is known to be unstable or even diverge when a nonlinear approximator is used to represent it, and there is no theoretical proof that such as convolutional neural network (CNN)-based deep network guarantees to converge to the correct Q-function for general applications. In an advantageous embodiment of the present invention, the training is supervised by instructing the agent to follow a greedy registration path, mimicking how humans register two objects in a most efficient manner. In particular, given the current transformation $m_t$ and the ground truth registration pose $m_g$, the optimal action $a_{t,o}$ at time t along the supervised registration path is defined as the action that minimizes the Euclidean distance between $m_t+a_{t,i}$ and $m_g$:

$$a_{t,o} = \min_{a_{t,i} \in A} \|m_g - (m_t + a_{t,i})\|_2. \qquad (5)$$

In an advantageous implementation, there are 6×2=12 candidate actions in the action set A, corresponding to the change of ±1 mm for each of the translation parameters [$t_x$, $t_y$, $t_z$] and ±1° for the orientation (rotation) parameters [$\theta_x$, $\theta_y$, $\theta_z$], meaning that the movement of the agent is restricted to be on the grid with a step size 1 in the transformation parameter space. By teaching the agent the registration path, the need to estimate Q through iterative update following the Bellman equation can be removed. Instead, the action-value Q function can be calculated explicitly via the following recursive function, assuming that the agent is allowed to run a sufficient number of steps to reach the ground truth pose $m_g$ following the supervised greedy path specified in Equation (5):

$$Q(s_t, a_{t,i}) = \begin{cases} r(s_t, a_{t,i}) + \gamma Q(s_{t+1,i}, a_{t+1,o}) & \text{if } \|m_{t+1,i} - m_g\|_2 > \epsilon \\ r(s_t, a_{t,i}) + R & \text{otherwise} \end{cases} \qquad (2)$$

where $$m_{t+1,i} = m_t + a_{t,i}, \qquad (7)$$

$$s_{t+1,i} = I_{ref} - I_{mov}(T_{m_{t+1,t}}).$$

and the immediate reward $r(s_t, a_{t,i})$ for action $a_{t,i}$(i=1,2, . . . 12) is proportional to the decrease of the distance of the transformation parameters to the ground truth pose $m_g$ by applying action $a_{t,i}$, $$r(s_t, a_{t,i}) = \|m_g - m_t\|_2 - \|m_g - m_{t+1}\|_2. \qquad (8)$$

The reward is discounted by a predetermined factor γ (e.g., γ=0.9) to implicitly include the number of steps as a cost, and the agent is considered to reach the correct pose and receives a bonus reward R (e.g., R=10) when it is within a predetermined tolerance $\epsilon$ (e.g., $\epsilon$=0.5) of the ground truth pose $m_g$ in the transformation parameter space.

It can be shown that if the agent is allowed to take the greediest path off the grid in the transformation parameter space to approach the ground truth pose $m_g$ with step size 1, i.e., the only constraint on the action is $\|a_{t,i}\|_2=1$, and the agent receives a proper bonus reward R when it reaches the target, then $Q(s_t, a_{t,o}) \geq Q(s_t, a_{t,i})$, meaning the trained agent can perform registration by simply choosing the action with the largest Q in the testing phase. In addition, $Q(s_t, a_{t,o})$ monotonically decreases with the increase in distance between $m_t$ and $m_g$, and approaches to a fixed value as the distance goes to infinity. Experimentally, it can be observed the following simplification of the Q-function: $Q(s_t, a_{t,i})=r(s_t, a_{t,i})$ without recursive calculation works equally well due to this property, i.e., the term $Q(s_{t+1,i}, a_{t+1,o})$ in Equation (6) quickly approaches to approximately a fixed offset that does not affect the selection of the optimal action at a given state.

A DNN is trained to represent the action-value Q-function in Equation (6). In an advantageous implementation, the DNN is a deep convolutional neural network CNN). The input to the DNN is the current state $s_t$, the output of the DNN has 12 nodes, each corresponding to one of the 12 actions in the action set A, and the loss function can be defined as:

$$\text{Loss} = \Sigma_{k=1}^{M} \Sigma_{i=1}^{12} \|y_i(s_k) - Q(s_k, a_{k,i})\|_2 \quad (9)$$

Where $y_i(s_k)$ is the i-th output of the CNN for the k-th sample among M training samples. The DNN (e.g., deep CNN) can be trained using a gradient descent algorithm and backpropagation to learn weights for layers of the DNN that minimize the loss function over all of the training samples. The DNN training scheme described herein has various advantages as compared to previous RL and DRL used in gaming applications. For example, the target Q-function described in the present disclosure is given analytically without iterative estimation, such that the network can be trained much more efficiently and with a more stable convergence property. In addition, the target Q calculation described herein does not require the exploration history of the agent, meaning that the data can be sampled arbitrarily randomly with little correlation, without the need for a large memory storage required by experience replay. These advantages are important to make this framework practical for 3D/3D registration applications dealing with large 3D volumes as input.

Labeled training image pairs (i.e., training image pairs with known ground truth transformations) of medical image may not be easy to obtain. According to an advantageous embodiment of the present invention, a limited set of labeled training data can be augmented to generate a large number synthetic training image pairs that can be used as training samples for training the DNN. In order to generate synthetic training image pairs, each of the aligned training image pairs with a known ground truth transformation can be artificially de-aligned by transforming one of the images with a set of transformations sampled in the transformation parameter space. For example, for each aligned training image pair, a predetermined number of rigid-body perturbations can be randomly generated within a predetermined range of each rigid-body transformation parameter. Since the original ground truth transformation is known, each of these transformation results in an additional training image pair for which the ground transformation is also known. In addition, for each aligned pair, denser sampling of the transformation parameter space close to the ground truth pose $m_g$ can be performed in order to train the DNN efficiently and reliably, because the network input-output mapping in this space is more complicated and less smooth as compared to that for the transformation parameter space far away from the ground truth aligned pose. In order to provide denser sampling of the transformation parameter space close to the ground truth transformation, each of the aligned training image pairs can be geometrically co-deformed by affine transformations $T_A$:

$$T_A = I + \begin{bmatrix} t_{11} & t_{12} & t_{13} & 0 \\ t_{21} & t_{22} & t_{23} & 0 \\ t_{31} & t_{32} & t_{33} & 0 \\ 0 & 0 & 0 & 1 \end{bmatrix} \quad (10)$$

where I is the 4×4 identity matrix and all the elements in $[t_{ij}]_{i=1,2,3, j=1,2,3}$ for shearing are independently and randomly generated within a predetermined range (e.g., [−0.25, 0.25]), to cover possible anatomical variations among patients in terms of sizes and shapes.

Figure 6:
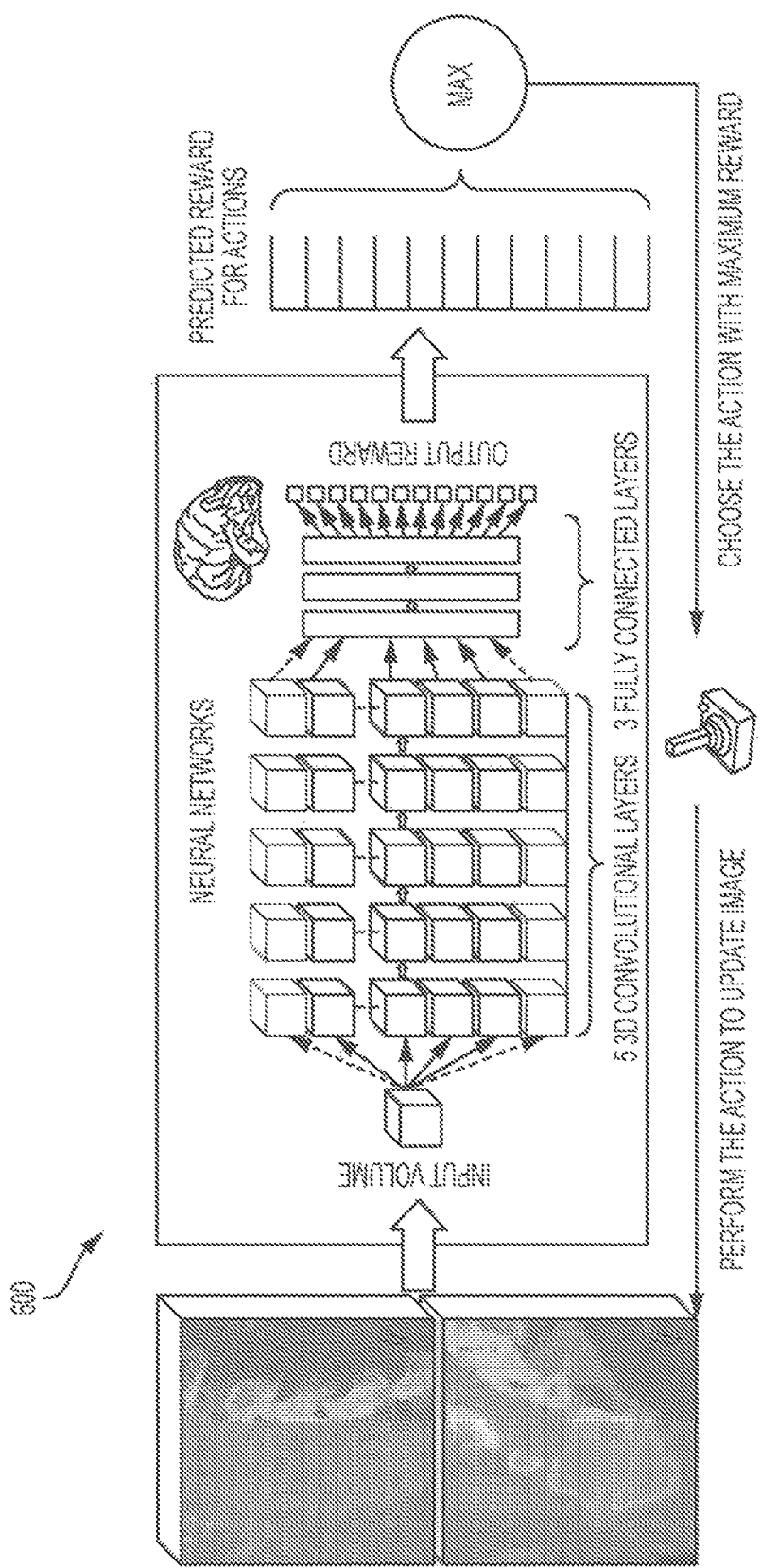
FIG. 6 illustrates and exemplary deep neural network (DNN) for rigid 3D/3D medical image registration according to an embodiment of the present invention.

The training (step 500 of FIG. 5) results in a trained DNN that predicts action-values (Q) for each of the set of actions based on the current state of the alignment of the images to be registered. FIG. 6 illustrates an exemplary DNN for rigid 3D/3D medical image registration according to an embodiment of the present invention. As shown in FIG. 6, the DNN 600 is a deep CNN with multiple hidden layers that inputs a 3D volume corresponding to the state of the alignment of the images $I_r$ and $I_f$ to be registered. In FIG. 6, $I_r$ is the reference image and $I_f$ is the moving or floating image. The input 3D volume is generated by subtracting $I_f$ transformed by the current rigid-body transformation parameters from $I_r$. In the example of FIG. 6, the DNN 600 has five 3D convolutional layers followed by three fully connected layers, but the present invention is not limited to this particular network structure. The output layer of the DNN 600 has 12 nodes, each corresponding to an action in the action set. In particular, the 12 output nodes represent the 12 candidate actions corresponding to adjustments of ±1 mm for each of the translation parameters $[t_x, t_y, t_z]$ and ±1° for the orientation (rotation) parameters $[\theta_x, \theta_y, \theta_z]$. The output nodes of the DNN 600 output predicted action-values/rewards for the corresponding actions. The intelligent artificial agent then selects the action with the highest predicted action-value and performs the action (i.e., the corresponding adjustment to the transformation) to update the transformation of the moving image $I_f$.

Returning to FIG. 5, at step 502, first and second medical images are received. For example, the first and second medical images can be images acquired using different imaging modalities (e.g., CT, MRI, ultrasound, PET, DynaCT, etc.), images of the same patient acquired at different times, or images acquired from different patients. The first and second medical images may be received directly from image acquisition devices, such as a CT scanner, MRI scanner, ultrasound device, C-arm image acquisition device, etc., or may be received by loading previously stored medical images from a memory or storage of a computer system or receiving the medical images in an electronic transmission from another computer system. One of the medical images is designated as the reference image $I_{ref}$ and the other is designated as the moving image $I_{mov}$. The method of FIG. 5 is described for 3D/3D registration, but can be similarly applied for 2D/2D registration as well.

At step 504, the current state is determined based on the current rigid body transformation parameters. In an advantageous implementation, the current state is determined by subtracting the moving image transformed by the current rigid-body transformation parameters, $I_{mov}(T_{m_t})$ from the reference image $I_{ref}$, i.e., using Equation (3). This results in a 3D state volume $s_t$. In the first iteration, before any of the rigid-body transformation parameters have been adjusted, the initial state can be calculated by subtracting the moving image $I_{mov}$ from the reference image $I_{ref}$ since no transformation has been applied to the moving image yet.

At step 506, action-values are calculated for each action in the set of possible actions based on the current state using the trained DNN. As described above, the set of possible actions includes actions corresponding to adjustments to each of the rigid-body transformation parameters. In particular, the set of possible actions can include 12 action actions corresponding to adjustments of ±1 mm for each of the translation parameters $[t_x, t_y, t_z]$ and ±1° for the orientation (rotation) parameters $[\theta_x, \theta_y, \theta_z]$. The trained DNN, such as the trained DNN 600 shown in FIG. 6, inputs the current state volume $s_t$ and calculates a predicted action-value (Q value) for each action.

At step 508, the action with the highest predicted action value is selected and the rigid-body transformation parameters are updated by performing the selected action. In an advantageous implementation, the selected action will adjust one of the translation parameters by ±1 mm or adjust one of the orientation parameters by ±1°. At step 510, the moving image is transformed using the updated rigid-body transformation parameters. At step 512, it is determined whether a stop condition has been met. For example, the stop condition can be met when it is determined that the transformation parameters have converged to a correct pose or when a predetermined maximum number of iterations have been performed. If the stop condition has not been met, the method returns to step 504 and repeats steps 504-512. Accordingly steps 504-512 are repeated until the stop condition is met. When the stop condition is met, the method proceeds to step 514.

At step 514, the registration result is output. The first and second medical images are registered by transforming the moving image by the final rigid-body transformation to align the moving image with the reference image. The registered first and second medical images can be output by displaying the registered first and second medical images on a display of a computer system. For example, the registered first and second images can be overlaid and displayed as a fused image. The registered first and second medical images can also be output by electronically transmitting the registered first and second images to a remote computer system to be displayed on a display of the remote computer system.

Although FIG. 5 only shows outputting the final registration result, it is also possible that the incremental registration results using the current rigid-body transformation parameters can be output (e.g., displayed on a display of a computer system) as each iteration of steps 504-512 is performed. Such incremental results would allow a user to view each adjustment made by the intelligent artificial agent to iteratively align the moving image to the fixed image in real-time as the artificial agent is registering the images.

Hierarchical Image Registration.

Since, in the case of 3D/3D registration, the input to the DNN is a large 3D volume instead of 2D images, the size of the volume is important for practical use. In order to achieve efficiency and accuracy, hierarchical image registration using multiple scale image data can be used. According to an advantageous embodiment of the present invention, two or more separate DNNs (e.g., deep CNNs) can trained at different image resolutions. For example, in the case of two resolutions, a first DNN can be trained with down-sampled volumes with a lower resolution, and a second DNN can be trained using high-resolution (i.e., original resolution without down-sampling) volumes. In an advantageous implementation, both of the first and second trained DNNs are trained using the same grid size (e.g., 64×64×64) volumes as the input but with different resolutions. The first DNN is trained for coarse alignment using down-sampled training volumes with a lower resolution, and focuses on robust alignment of an object in the images to be registered even when the initial displacement is large. The second DNN is trained using high-resolution training volumes with a limited field of view (FOV) and focuses on aligning the object as accurate as possible despite the limited FOV. The first and second DNNs are each trained as described above in connection FIG. 1 and/or FIG. 5. For example, each of the first and second trained DNNs can have network architecture similar to the DNN 600 of FIG. 6. The trained first and second DNNs are then used for hierarchical image registration of newly received images. This hierarchical registration can be applied to any type of registration approach (e.g., rigid, affine, deformable) and any dimensionality (e.g., 2D/2D, 3D/3D. etc.).

Figure 7:
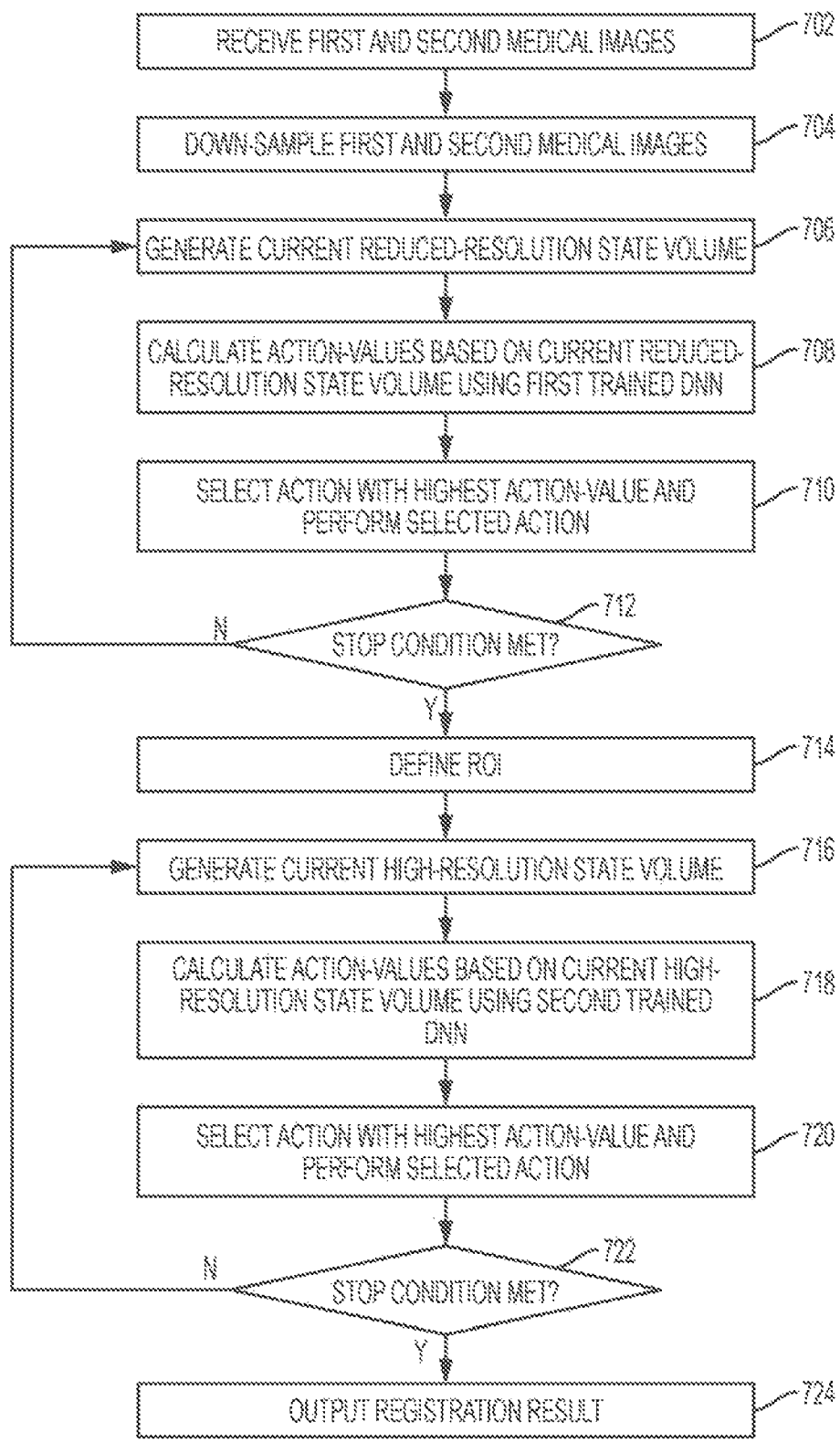
FIG. 7 illustrates a method of hierarchical image registration using multi-scale image data according to an embodiment of the present invention.

FIG. 7 illustrates a method of hierarchical image registration using multi-scale image data according to an embodiment of the present invention. At step 702, first and second medical images are received. For example, the first and second medical images can be images acquired using different imaging modalities (e.g., CT, MRI, ultrasound, PET, DynaCT, etc.), images of the same patient acquired at different times, or images acquired from different patients. The first and second medical images may be received directly from image acquisition devices, such as a CT scanner, MRI scanner, ultrasound device, C-arm image acquisition device, etc., or may be received by loading previously stored medical images from a memory or storage of a computer system or receiving the medical images in an electronic transmission from another computer system. One of the medical images is designated as the reference image $I_{ref}$ and the other is designated as the moving image $I_{mov}$. The method of FIG. 7 is described for 3D/3D registration using a rigid-body transformation, but can be similarly applied for 2D/2D registration and/or for other types of transformation parameterizations.

At step 704, the first and second medical images are down-sampled to generate first and second reduced-resolution images. Various well-known down-sampling techniques can be used to down-sample the first and second medical images.

At step 706, a current reduced resolution state volume is generated using the first and second reduced resolution images and the current transformation parameters. The current reduced resolution state volume can be determined by subtracting the reduced-resolution moving image transformed by the current transformation parameters from the reduced resolution reference image. At step 708, action-values are calculated for each of the actions in the set of possible actions using the first trained DNN. As described above, the set of possible actions can include actions corresponding to adjustments to each of the rigid-body transformation parameters. In particular, the set of possible actions can include 12 action actions corresponding to adjustments of ±1 mm for each of the translation parameters $[t_x, t_y, t_z]$ and ±1° for the orientation (rotation) parameters

[$\theta_x$, $\theta_y$, $\theta_z$]. The first trained DNN, which is trained using down-sampled reduced resolution images, inputs the current reduced-resolution state volume calculated from the first and second reduced resolution images and calculates a predicted action-value (Q value) for each action. At step 710, the action with the highest action value is selected and the transformation parameters are updated by performing the selected action.

At step 712, it is determined whether a stop condition is met. In an exemplary embodiment, the stop condition for registration using the first trained DNN is met when a first predetermined number $N_1$ of iterations using the first trained DNN have been performed. In this case, if $N_1$ iterations using the first trained DNN have not yet been performed, the stop conditions has not yet been met and the method returns to step 706 and repeats steps 706-712. Accordingly, steps 706-712 are repeated until $N_1$ iterations using the first trained DNN are performed. When $N_1$ iterations have been performed using the first trained DNN, the stop condition has been met and the method proceeds to step 714. In an exemplary implementation, $N_1$=200, such that 200 sequential actions are applied based on the reduced resolution images using the first trained DNN in order to roughly align the images. In other embodiments, other stop conditions for the registration using the first trained DNN may be used. For example, the stop condition may be met when the registration using first trained DNN achieves a predetermined accuracy threshold (e.g., an error value between the reduced-resolution reference image and the transformed reduced-resolution moving image is less than a threshold), when the registration using the first trained DNN converges (e.g., the transformation parameters converge or an error value between the reduced-resolution reference image and the transformed reduced-resolution moving image converges), or in a case in which the first trained DNN includes a "stop" action, when the "stop" action is the selected as the action having the highest action value. Other stopping criteria, such as when loops in actions are detected, may be used as well.

At step 714, a region of interest (ROI) is defined based on the first trained DNN. The reduced resolution state volume is updated based on the current transformation parameters. A single back-propagation pass is then used to compute the derivative of the sum of the outputs of the layers of the first trained DNN with respect to the input reduced resolution state volume, resulting in a saliency map of the input reduced resolution state image. The resulting saliency map is then thresholded, for example using $95^{th}$ percentile thresholding, and the weighted mean is calculated on the thresholded saliency map to localize an ROI to be used for the input to the second trained DNN.

At step 716, a current high-resolution state volume is generated using the first and second medical images and the current transformation parameters and the defined ROI is extracted from the current high-resolution state volume. The current high-resolution state volume can be generate by subtracting the original resolution moving image transformed by the current transformation parameters from the original resolution reference image. The ROI defined step 714 is then extracted from the current high-resolution state volume. At step 718, action-values are calculated for each of the actions in the set of possible actions using the second trained DNN based on the ROI of the current high-resolution state volume. The set of possible actions can include actions corresponding to adjustments to each of the rigid-body transformation parameters. In particular, the set of possible actions can include 12 actions corresponding to adjustments of ±1 mm for each of the translation parameters [$t_x$, $t_y$, $t_z$] and ±1° for the orientation (rotation) parameters [$\theta_x$, $\theta_y$, $\theta_z$]. The second trained DNN, which is trained using high resolution images in a limited FOV, inputs only a portion of the current high-resolution state volume corresponding to the ROI defined in step 714, and calculates a predicted action-value (Q value) for each action. Since the ROI is defined based on the saliency map of the first trained DNN, the ROI focuses the second trained DNN on the most salient portions of the input volume for image registration. At step 720, the action with the highest action value is selected and the transformation parameters are updated by performing the selected action.

At step 722, it is determined whether a stop condition has been met. In an exemplary embodiment, the stop condition for registration using the second trained DNN is met when a second predetermined number $N_2$ of iterations have been performed using the second trained DNN. In this case, if $N_2$ iterations have not yet been performed using the second trained DNN, the stop condition has not been met and the method returns to step 716 and repeats steps 716-722. Accordingly, steps 716-722 are repeated until $N_2$ iterations are performed using the second trained DNN. When $N_2$ iterations have been performed using the second trained DNN, the stop condition has been met and the method proceeds to step 724. In an exemplary implementation, $N_2$=100, such that 100 sequential actions are applied using the second trained DNN. In other embodiments, other stop conditions for the registration using the second trained DNN may be used. For example, the stop condition may be met when the registration using second trained DNN achieves a predetermined accuracy threshold (e.g., an error value between the reference image and the transformed moving image is less than a threshold), when the registration using the second trained DNN converges (e.g., the transformation parameters converge or an error value between the reference image and the transformed moving image converges), or in a case in which the second trained DNN includes a "stop" action, when the "stop" action is the selected as the action having the highest action value. Other stopping criteria, such as when loops in actions are detected, may be used as well.

At step 724, the registration result is output. The first and second medical images are registered by transforming the moving image by the final rigid-body transformation to align the moving image with the reference image. The registered first and second medical images can be output by displaying the registered first and second medical images on a display of a computer system. For example, the registered first and second images can be overlaid and displayed as a fused image. The registered first and second medical images can also be output by electronically transmitting the registered first and second images to a remote computer system to be displayed on a display of the remote computer system.

Although FIG. 7 only shows outputting the final registration result, it is also possible that the incremental registration results using the current transformation parameters can be output (e.g., displayed on a display of a computer system) as each iteration of steps 704-710 and each iteration of steps 716-722 is performed. Such incremental results would allow a user to view each adjustment made by the intelligent artificial agent in real-time as the artificial agent is registering the images The present inventors evaluated the above described embodiments for 3D/3D rigid medical image registration on registration of abdominal spine CT and cone beam CT (CBCT) images and registration of cardiac CT and CBCT images. In abdominal spine CT and CBCT registration, a main challenge is that CT has a much larger view that CBCT, leading to many local optima in the registration space due to the repetitive nature of the spine. 87 image pairs were used for the abdominal spine CT and CBCT registration, with 82 image pairs used for training and 5 pairs used for testing. In cardiac CT and CBCT registration, a main challenge is the poor quality of CBCT with severe streaking artifacts and weak soft tissue contrast at the boundary of the object to be registered, i.e., the epicardium. 97 image pairs were used for the cardiac Ct and CBCT registration, with 92 pairs used for training and 5 pairs used for testing. Expert manual annotations on spine landmarks and mesh delineation at the epicardium were used to run iterative closest point (ICP)-based registration followed by visual inspection to provide the ground truth alignment for the spine and cardiac image pairs, respectively.

The same network architecture was used for the DNN for both the spine and cardiac applications and both registration layers, as follows. The DNN trained for each application includes five convolutional layers followed by three fully connected layers. The five convolutional layers use 8, 32, 32, 128, and 128 filters, respectively, all with 3×3×3 kernels. The first two convolutional layers are each followed by a 2×2×2 max-pooling layer. The three fully connected have 512, 512, and 64 activation neurons, respectively, and the output has 12 nodes corresponding to the twelve possible actions in A. Each layer is followed by a non-linear rectified layer, and batch normalization is applied to each layer. During training, each training image pair was augmented 64,000 times, leading to >5M training samples for each application. To train the DNN for coarse registration, rigid-body perturbation was randomly generated within [±30 mm, ±30 mm, ±30 mm, ±30°, ±30°, ±30°] for the cardiac data and [±30 mm, ±30 mm, ±150 mm, ±30°, ±30°, ±30°] for the spine data to cover the large FOV in the head-foot direction in the spine CT. In addition, with a probability of 0.2, rigid-body perturbation was randomly generated within [±10 mm, ±10 mm, ±10 mm, ±10°, ±10°, ±10°], in order to more densely sample the transformation parameter space close to the correct alignment. To train the CNN for refinement registration, the rigid-body perturbation range was reduced to [±5 mm, ±5 mm, ±5 mm, ±5°, ±5°, ±5°]. The DNN (both for coarse alignment and for refinement registration) was trained using RMSprop gradient descent update without momentum and a batch size of 32. The learning rate was 0.00006 with a decay of 0.7 every 1000 mini-batch based back propagations. For each case, the training took approximately 24 hours on a single GeForce Titan X.

Figure 8:
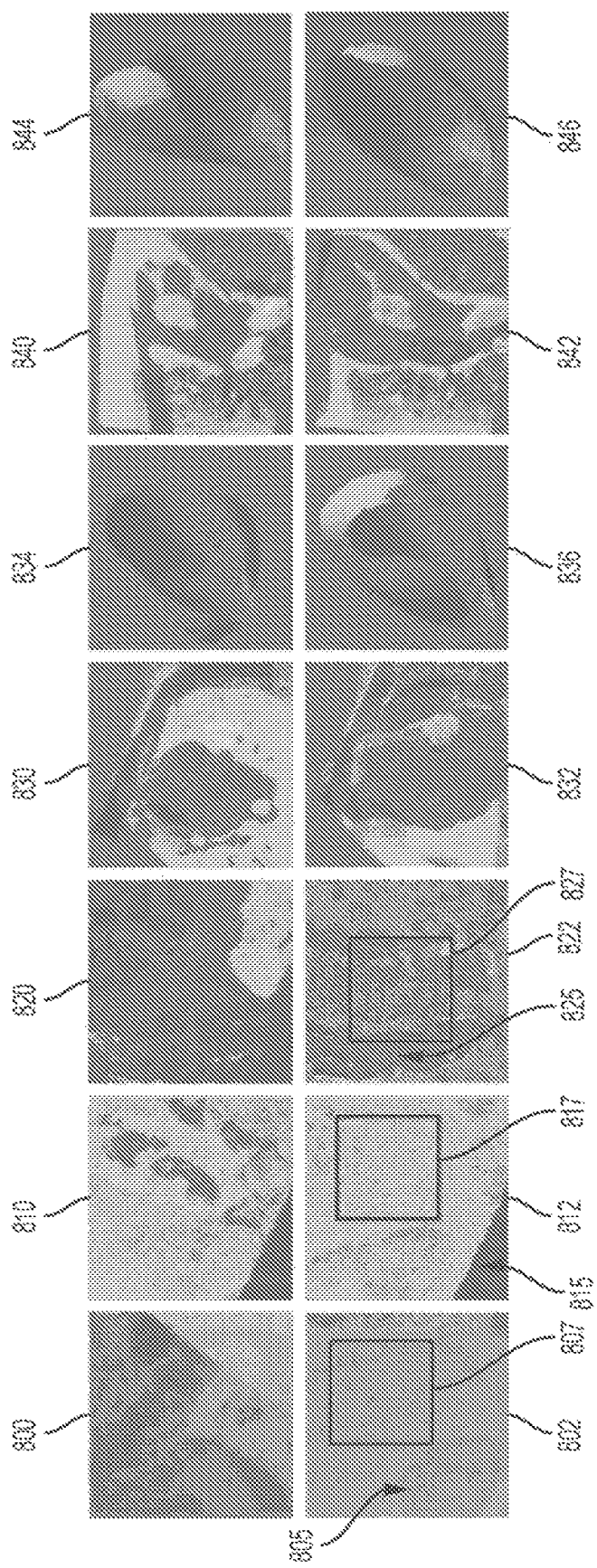
FIG. 8 illustrates exemplary registration results for spine computed tomography (CT) and cone beam CT (CBCT) registration and cardiac CT and CBCT registration.

FIG. 8 illustrates exemplary registration results for spine CT and CBCT registration and cardiac CT and CBCT registration. FIG. 8 shows registration results for three spine CT and CBCT registration examples and two cardiac CT and CBCT registration examples. As shown in FIG. 8, images 800 and 802 show the difference between the reference and moving images (i.e., the state image) before and after registration, respectively, for a first spine CT and CBCT registration example. Images 810 and 812 show the difference between the reference and moving images before and after registration, respectively, for a second spine CT and CBCT registration example. Images 820 and 822 show the difference between the reference and moving images before and after registration, respectively, for a third spine CT and CBCT registration example. Arrows 805, 815, and 825 in the first, second, and third spine CT and CBCT registration examples, point to the kidney, the black background outside the imaged volume, and deployed stent graphs, respectively, showing the high robustness of the intelligent agent in dealing with various interfering objects and artifacts during registration. Hierarchical registration using the method of FIG. 7 was applied to each spine example, and boxes 807, 817, and 827 show the detected ROI at which the attention was focused in the refinement registration using the second trained DNN for the first, second, and third spine CT and CBCT examples, respectively. As shown in FIG. 8 images 830 and 832 show the difference between the reference and moving images before and after registration, respectively, for a first cardiac CT and CBCT registration example. Images 834 and 836 show the mesh overlay for the epicardium meshes in the CT and CBCT images before and after registration, respectively, for the first cardiac CT and CBCT registration example. Images 840 and 842 show the difference between the reference and moving images before and after registration, respectively, for a second cardiac CT and CBCT registration example. Images 844 and 846 show the mesh overlay for the epicardium meshes in the CT and CBCT images before and after registration, respectively, for the second cardiac CT and CBCT registration example.

Figure 9:
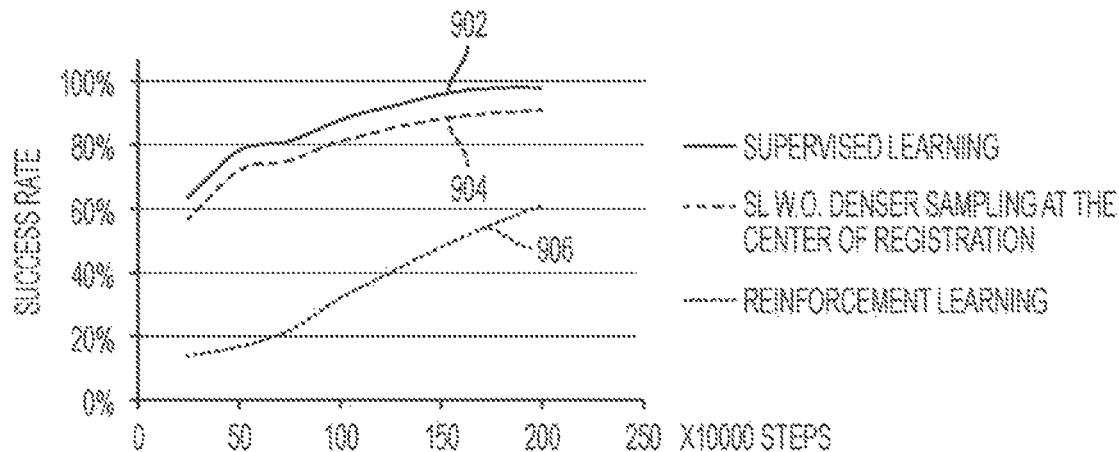
FIG. 9 illustrates a comparison of supervised deep reinforcement learning and unsupervised deep reinforcement learning for 2D/2D spine image registration.

The present inventors evaluated the efficiency of the supervised deep RL described herein in comparison with deep RL without supervision on a modified 2D/2D registration problem using the spine data, due to the un-affordable large memory storage required by experience replay in the unsupervised RL for 3D/3D registration. In the modified 2D/2D registration problem, 2D multiplanar reconstruction (MPR) image pairs were extracted from 82 aligned CT and CBCT spine pairs using various MPR cuttings. For the supervised learning (SL), these 2D images were artificially de-aligned in 2D by random perturbations within [±30 mm, ±30 mm, ±30°] to generate 2M image pairs for training. The network architecture was modified from the 3D/3D registration examples to take 128×128 2D images as the input, and the output has six nodes corresponding to 6 possible actions in changing $[t_x, t_y, \theta_z]$. The network architecture and training hyper-parameters were the same for SL and unsupervised RL. For SL, the present inventors also compared the training efficiency and accuracy with and without denser sampling of the transformation parameter space close to the ground truth alignments. FIG. 9 illustrates a comparison of supervised deep reinforcement learning (SL) and unsupervised deep reinforcement learning for the 2D/2D spine registration. FIG. 9 shows a plot of success rate versus the number of training steps for the 2D/2D spine registration using supervised learning (SL) 902, supervised learning without denser sampling 904, and unsupervised RL 906. It can be seen from FIG. 9 that SL is much more efficient than unsupervised RL and achieves significantly better results when the same number of training data are used. In addition, proper data distribution in training samples (by denser sampling close to the ground truth alignments) is shown to be beneficial for the agent to learn the complex mapping efficiently.

Deformable Registration of Medical Images Used Intelligent Artificial Agent

In an advantageous embodiment of the present invention, an intelligent artificial agent is used to perform deformable registration of medical images. A major difficulty in medical image registration is incorporating non-rigid deformations, which frequently occur in medical imaging due to different patient positioning, pathological and physiological changes (e.g. empty vs. filled bladder), and/or cardiac and respiratory motion. Current deformable registration algorithms based on variational approaches try to counter such problems in finding a transformation that maps one image to the other by solving an objective function typically consisting of a similarity measure (e.g., SSD, mutual information) and differently motivated regularizers (e.g., elastic, fluid, curvature-based models). However, these approaches have difficulties in modeling large deformations and sliding motions along the boundaries of different tissues, such as the lungs. Furthermore, the existing algorithms are engineered for specific applications and do not generalize well for other registration applications. By using deep-learning systems with automated feature design, embodiments of the present invention can overcome these limitations through learning the intrinsic and complex mapping in the spatial and intensity domain. Embodiments of the present invention utilize artificial deep neural networks to extract features from both objects/images to be registered and compare them to assess the similarity, followed by a prediction of an optimal way to change the features of one image should be changed to get closer to the other image. This pattern is applied in a step-by-step approach to approximate the registration in a coarse-to-fine manner. Embodiments of the present invention combine an efficient encoding/decoding of the deformation field with an intelligent artificial agent based trajectory learning that predicts parametric actions operating on the encoded parameters.

Figure 10:
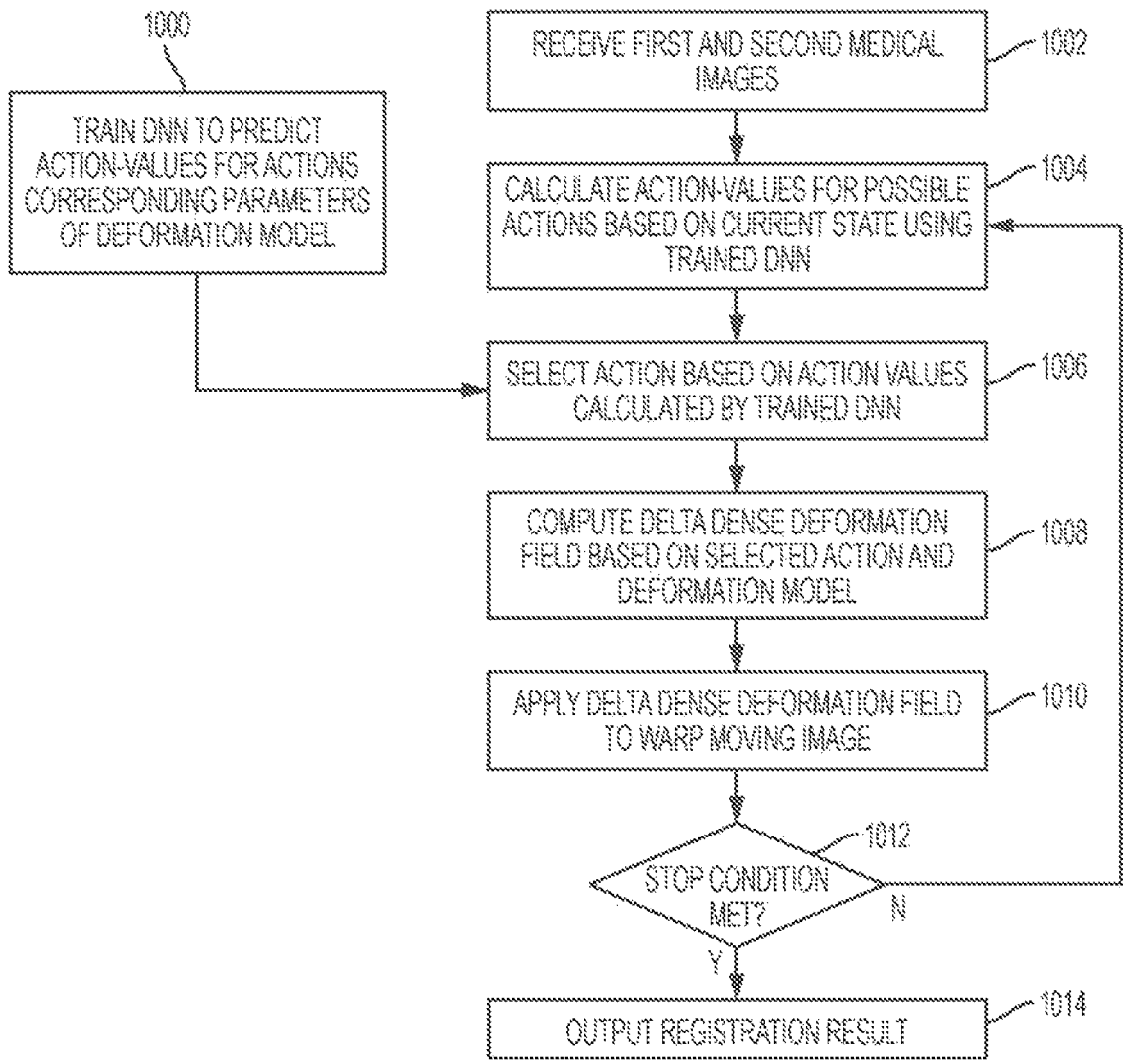
FIG. 10 illustrates a method for deformable registration of medical images using an intelligent artificial agent according to an embodiment of the present invention.

FIG. 10 illustrates a method for deformable registration of medical images using an intelligent artificial agent according to an embodiment of the present invention. The method of FIG. 10 can be applied to any deformable (non-rigid) registration task. For example, the method of FIG. 10 can be used for applications including, but not limited to, contour propagation between different medical imaging modalities or atlas-based segmentation (in which segmentation is performed by registering an atlas to a medical image a patient) for therapy planning. In contrast to other current deformable registration methods, the method of FIG. 10 is not engineered for a specific application and can be used to perform deformable registration in problematic cases, such as cases involving large deformations or sliding motion.

Referring to FIG. 10, at step 1000, a DNN is trained to predict action-values for a set of actions corresponding to parameters of a deformation model used to encode a deformation field. Step 1000 is performed in an offline training stage prior to the on-line image registration for newly input/received images performed in steps 1002-1014. The DNN is trained to predict action-values for the actions based on a reward function that evaluates the current state of the system.

Figure 11:
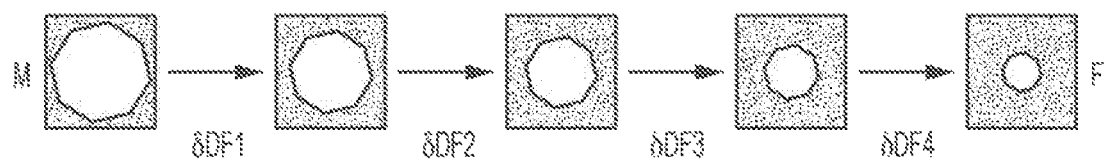
FIG. 11 an exemplary idealized deformation trajectory between a moving image and a fixed image.

In an advantageous embodiment of the present invention, supervised trajectory learning is used to train the DNN. As the ground truth flow field (image deformation field) between two images is typically not available for real medical images, supervised trajectory learning is used to train the DNN to learn steps on the trajectory of small deformations to reach the final deformation field and reward actions corresponding to the small deformations on the learned trajectory. Thus, at each iteration, a small deformation flow field ($\delta DF$), which is the outcome of taking one of the best actions based the rewards (action-values) computed by the agent-based network (DNN) and applying the action in the encoded dense deformation field space, is applied to the moving image to warp the moving image to be closer to the fixed image. In an advantageous implementation, the action selection can be performed in a probabilistic way to enable the intelligent artificial agent to not always select the best action in a specific state and allow circuitous routes to avoid local minima ($\epsilon$-greedy selection). In this case, the probability of each action being selected is based on the action-value (reward) predicted for that action by the DNN. The composition of all of the $\delta DF$s over all of the iterations results in the final flow field that warps the moving image to register the moving image to the fixed image. FIG. 11 an exemplary idealized deformation trajectory between a moving image M and a fixed image F. As shown in FIG. 11, in each iteration the artificial intelligent agent selects an action based on the current reward determined by the DNN and applies the $\delta DF$ corresponding to the selected action to warp the moving image M. In FIG. 11, the moving image is registered to the fixed image F over four iterations, and the composition of $\delta DF_1$, $\delta DF_2$, $\delta DF_3$, and $\delta DF_4$ result in the final flow field that registers the moving image M with the fixed image F.

Figure 12:
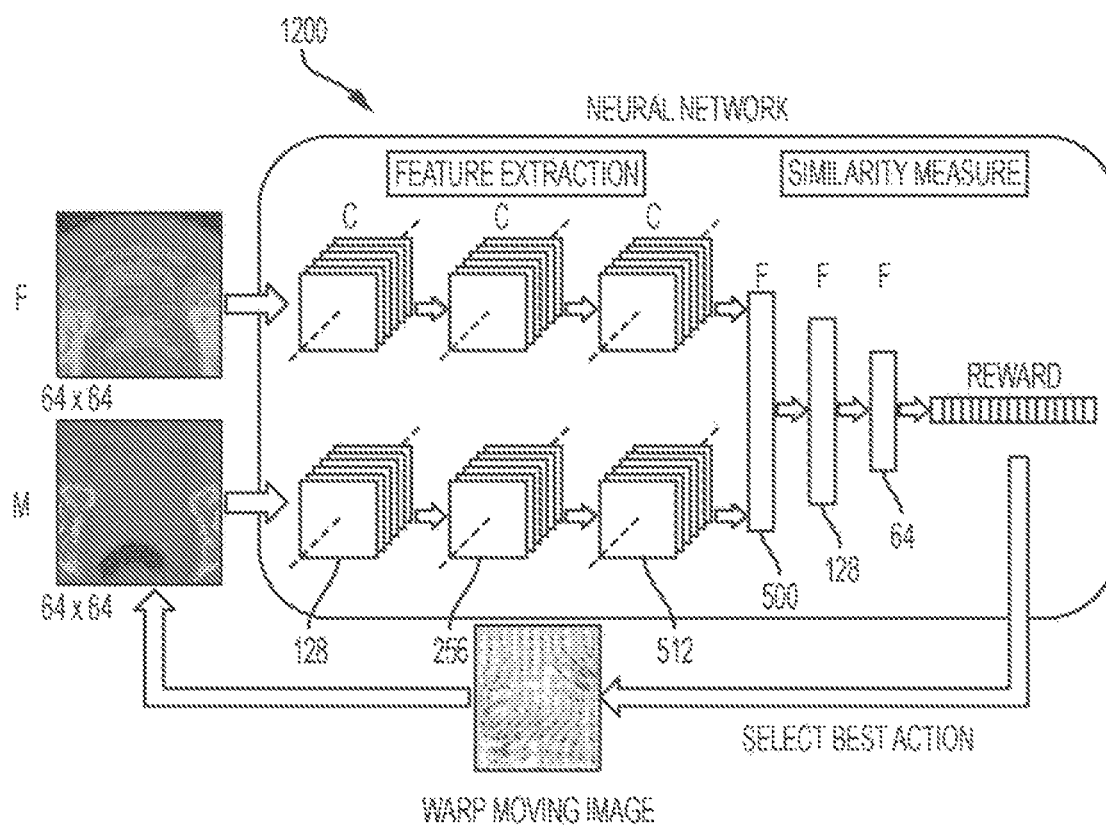
FIG. 12 illustrates an exemplary DNN for deformable image registration according to an embodiment of the present invention.

FIG. 12 illustrates an exemplary DNN for deformable image registration according to an embodiment of the present invention. As shown in FIG. 12, the DNN 1200 inputs a fixed image F and a moving image M. In the embodiment of FIG. 12, the DNN 1200 takes 64×64 2D images as input, but the present invention is not limited thereto. Features of both images are extracted with separate but identical, in points of network architecture, processing streams. In particular, the CNN 1200 uses multiple convolutional layers, whose weights are not shared between the fixed/reference image stream and the moving image stream, for feature extraction. That is separate weights are learned for the convolutional layers that extract features from the fixed image F and the convolutional layers that extracted features from the moving image M. In the embodiment of FIG. 12, the CNN 1200 includes three convolutional layers that use 128, 256, and 512 filters, respectively, in each of the fixed image stream and the moving image stream. The convolutional layers used for feature extraction are followed by fully connected layers, at which the extracted features from the fixed and moving images are compared at a higher level to compute reward values for various possible actions. The fully connected layers act as a learned similarity measure based on the features extracted from the fixed and moving images. In the embodiment of FIG. 12, the CNN 1200 includes three fully connected layers having 500, 128, and 64 activation neurons, respectively. An action prediction is retrieved/selected based on the action-values (rewards) output by the DNN 1200, and the action prediction can then be transferred to a low-dimensional deformation encoding. Dense prediction follows from decoding the few parameters of the encoded action to a delta dense deformation field ($\delta DF$) with help from a chose parametric deformation model. The $\delta DF$ is then directly applied on the moving image to warp the moving image. Dependent on the training data, the reward may be computed directly at the level of encoded components. The DNN framework is trained to predict the next best action based on the current state (determined by the feature extraction from the fixed and moving images) from available actions corresponding to +/− adjustments on the encoded parameters (i.e., the parameters of the parametric deformation model). Coarse-to-fine support may be given by joining actions that are "similar" in parametric space to enable faster convergence, avoid unrealistic states, and reduce dimensionality of otherwise huge parametric spaces. For training of the DNN, the loss function can be computed as:

$$\text{Loss}(s, a, s') = \frac{1}{B} \sum_i^B (r_{GT} - R(s, a, s'))^2 \quad (11)$$

where s is the current state, a is the action, s' is the next state if the agent takes action a from state s, $r_{GT}$ is the known ground truth reward, R is the learned reward computed by the trained DNN, and B is the number of landmarks or mesh points on the contour or surface being deformed. The DNN can be trained using a gradient descent algorithm and backpropagation to learn weights for layers of the DNN that minimize the loss function over all of the training samples.

Figure 13:
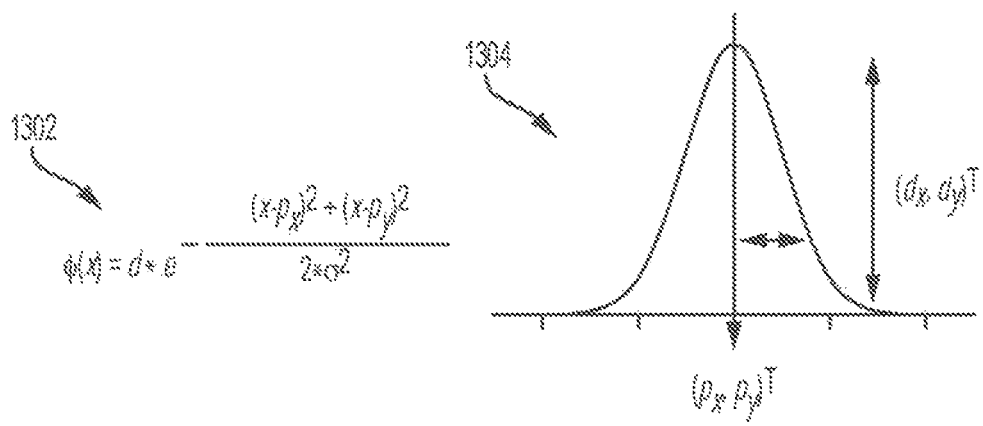
FIG. 13 illustrates a Gaussian radial basis function (RBF)

A deformation model is used to encode the dense deformation field in order to reduce the dimensionality of the dense deformation field. In one embodiment of the present invention, a parametric deformation model whose parameters are applicable for smooth transitions from one state to its neighbor can be used to encode the dense deformation field. Radial Basis Functions (RBF) are an example of such a parametric deformation model that can be used to encode dense deformation field. FIG. 13 illustrates a Gaussian RBF. As shown in FIG. 13, the Gaussian RBF 1302 can be expressed as $$\phi(x) = d * e^{-\frac{(x-p_x)^2+(x-p_y)^2}{2*\sigma^2}}.$$

The Gaussian RBF 1302 models the deformation of pixels in a neighborhood of a location ($p_x$, $p_y$) as having a Gaussian distribution 1304 centered as ($p_x$, $p_y$) with magnitude d=($d_x$, $d_y$) and standard deviation σ. The Gaussian RBF 1302 computes the deformation φ at a point x based on the distance of x from the location ($p_x$, $p_y$), the magnitude d=($d_x$, $d_y$), and the standard deviation σ. In a possible implementation, multiple Gaussian RBFs can be used to approximate the dense deformation field for the moving image. In this case the set of possible actions can correspond to adjustments to the Gaussian parameters, such as location and magnitude, for each of the Gaussian RBFs.

In another embodiment, a free form deformation (FFD) approach can be used to encode the dense deformation field. In this case, the DDN learns the desired action for moving a limited number of points of a uniform hull while preserving topology. Dense deformation inside the whole is approximated, for example using B-splines or thin plate splines (TPS). In this model, the agent can learn actions that directly modify the B-splines parameters (e.g., direction, amplitude, and extent of the displacement at the B-spline node). In another embodiment, all B-spline parameters are projected onto a subspace representation (e.g. via PCA or any other manifold learning method) and the agent directly modify the transformation parameters in the subspace (e.g. by normalized increment/decrement along a PCA mode).

In another embodiment, various types of manifolds that reduce the dimensionality of the action space through encoding the dense deformation field can be used as the deformation model. In this case, the action space of deformations is learned from a set of training examples using manifold learning (linear or non-linear). Multiple possibilities exist for this purpose, such as principal component analysis (PCA), stacked denoising autoencoder, or deep learning based generative models. The agent actions are performed directly on the subspace parameters (e.g., via PCA or any other manifold learning method). The agent directly modifies the transformation parameters in the subspace (e.g., by normalized increment/decrement along a PCA mode) and the resulting deformation field is reconstructed from the updated subspace parameterization.

The deformation model can be dense model or a correspondence based model. In one embodiment, the deformation model is a dense model. In this case, the deformation model encodes the entire dense deformation field of the moving image (or image region/image patch) to be registered. For a dense model, in additional the two input images (i.e., fixed and moving images) in each training image pair, ground truth delta deformation fields δDFs are used to train the encoder/decoder and the DNN. δDFs can be small deformation updates or, in the case of diffeomorphic deformation, stationary velocity field updates or even kinetic moment updates in the case of time-varying velocity field representation of the deformation, like in the Large Deformation Diffeormophic Metric Mapping (LDDMM). As only small deformation fields (resulting from applying one action) are required, the ground truth δDFs can be obtained from existing deformable registration algorithms. According to an advantageous implementation, to avoid learning possible insufficient deformation fields resulting from such existing deformable registration algorithms, the algorithm's output can be used to produce a new warped version of the fixed image (generated by warping the moving image by the deformation field output by the algorithm) which can be used in the training instead of the original fixed image. The new fixed training image may be different that the original fixe training image, but by applying this scheme it is guaranteed that the real ground truth deformation field is used for training, as long as any reasonable deformation field is provided by the existing deformable registration algorithm used.

In another embodiment, the deformation model is a correspondence based model. In this case, the deformation model encodes a sparse deformation field corresponding to deformations of the particular points (e.g., landmarks or control points) or structures in the moving image that having correspondences in the fixed image. In addition to the two input images (i.e., fixed and moving images) of each training image pair, point correspondences or segmentations of deforming structures in the images are also used for training. The segmentations can be performed manually, automatically, or semi-automatically using various segmentation algorithms. In the case of precise segmentations, exact point correspondences exist and can be used as the ground truth spare deformation field for training. It is also possible to establish point correspondences between the fixed and moving images in the training image pairs using a ray-shooting algorithm. Given a segmentation mask, in order to retrieve distributed points on the surface of a convex structure of interest, a ray-shooting algorithm can be performed that shoots rays from the center of mass to the surface with equal angular distances and selects the points where the rays leave the mask as landmark positions. By applying this procedure, the topology of landmarks is guaranteed. If the landmark positions are extracted in the same way across the whole training data set, the DNN learns the topology in training and may learn to connect rewards to specific landmarks. Once the sparse deformation field for the point correspondences is obtained, the dense flow field can be obtained by interpolation and extrapolation, for example using RBFs. In another possible implementation, a neural network, such as an autoencoder, can be trained to find a mapping between the sparse deformation field and the dense flow field.

Figure 14:
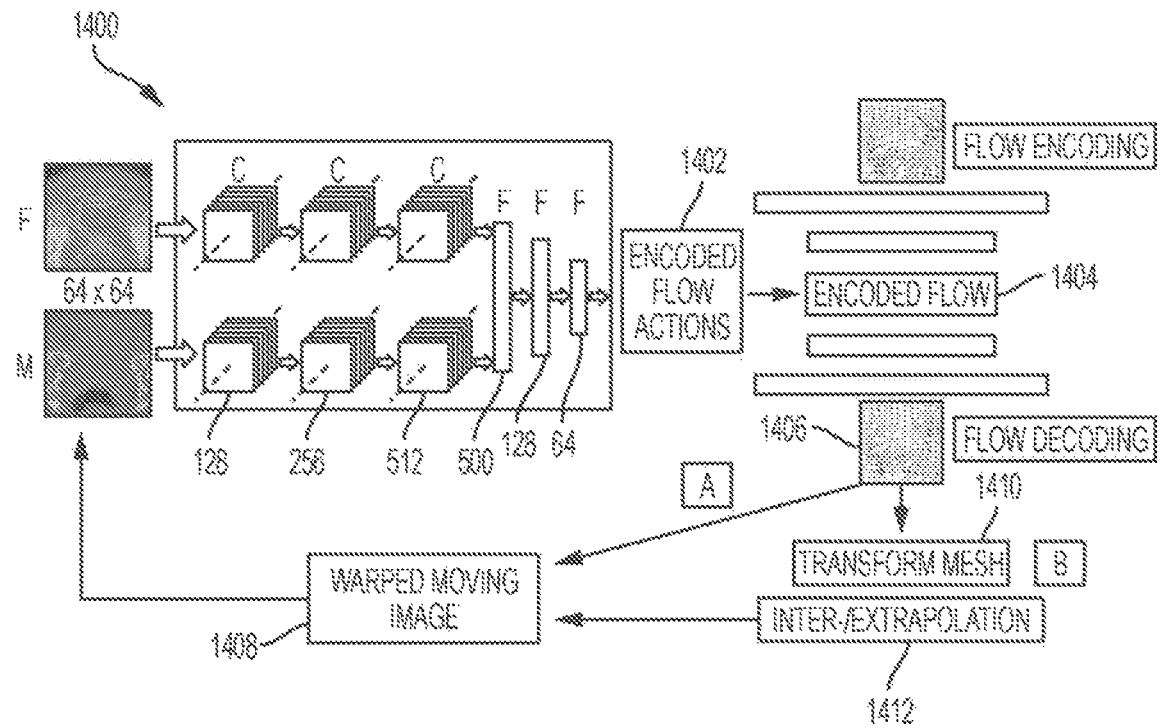
FIG. 14 illustrates a framework for decoding encoded flow actions output from a trained DNN according to an embodiment of the present invention.

FIG. 14 illustrates a framework for decoding encoded flow actions output from a trained DNN according to an embodiment of the present invention. As shown in FIG. 14, a fixed image F and a moving image M are input to the trained DNN 1400. The DNN 1400 extracts features from the fixed and moving images and predicts best flow action based on the current state of the fixed and moving images. A deformation model is selected for flow encoding, and the trained DNN 1400 outputs encoded flow actions 1402 in the parameter space/component space of the deformation model used for the flow encoding. The encoded flow action 1402 performed to adjust the encoded flow 1404, and flow decoding is performed to decode the encoded flow 1404 into a decoded flow field 1406. Path A represents the case in which the deformation model is a dense model. In this case, the decoded flow field 1406 is a dense deformation field and is applied to the moving image generate the warped moving image 1408, which is input to the DNN 1400 as the moving image M for the next iteration. Path B represents the case in which the deformation model is correspondence based model. In this case, the decoded flow field is used to transform a mesh (1410) of a segmented structure in the moving image. A dense deformation field is then computed based on the deformation of the mesh using interpolation and/or extrapolation (1412), and the dense deformation field is applied to the moving image to generate the warped moving image 1408, which is input the DNN 1400 as the moving image M for the next iteration.

The action design is highly related to the chose encoding method. In particular, for each type of deformation model that can be used for the encoding, a set of actions can be defined to by small adjustments (+/−) to various parameters or components of that deformable model. In an advantageous embodiment, RBFs, such as Gaussian functions are used and a subspace of their parameters space is used as the action space. For example, the location (mean) and magnitude parameters of the Gaussian RBFs can be used to define the set of actions. In particular, the set of actions can be include +/− predetermined adjustments of the location (mean) and magnitude parameters for each Gaussian RBF used to model the deformation of the moving image.

Figure 15:
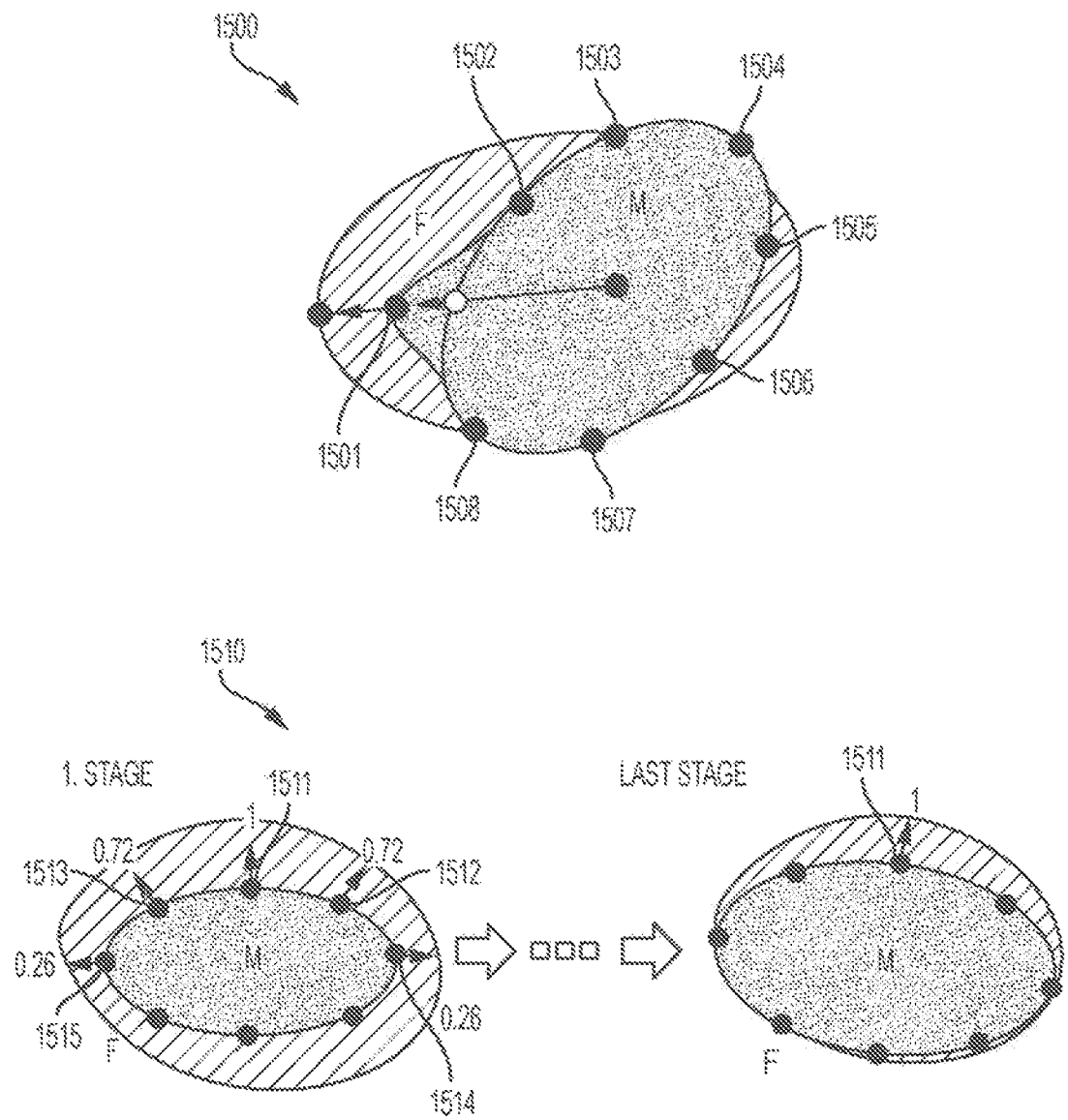
FIG. 15 illustrates examples of deforming a contour of an organ of interest using Gaussian kernels.

In an advantageous implementation, Gaussian kernels can be placed at landmark positions in the moving image, such as at control points on a contour or mesh of a segmented organ of interest, and the agent can be driven to align the contours of the of the organ of interest as in an FFD approach. FIG. 15 illustrates examples of deforming a contour of an organ of interest using Gaussian kernels. As shown in example 1500 of FIG. 15, contour F represents a contour of a segmented target organ in the fixed image and contour M represents a contour of the segmented target organ in the moving images. Gaussian kernels are placed at each of a plurality of landmarks 1501, 1502, 1503, 1504, 1505, 1506, 1507, and 1508 and the parameters of the Gaussian kernels are adjusted to iteratively deform contour M to align contour M with contour F. Coarse-to-fine registration can be reached by combining or joining neighboring Gaussian kernels and moving them together, such as in Example 1510 of FIG. 15. That is when an action is selected to move a Gaussian kernel at one landmark point, the Gaussian kernels at neighboring landmark points may be moved as well. The magnitude of movement can be controlled by a separate Gaussian process such that movements of the neighboring Gaussian kernels decrease with a distance to the chose Gaussian kernel. Neighbor relationships can be fixed by predefining the topology. In order to achieve coarse-to-fine registration, when the contour in the moving image is close to the contour in the fixed, the Gaussian kernels may be moved without the joint movement of the neighboring Gaussian kernels. As shown in example 1510 of FIG. 15, in a first stage of deforming the contour M in the moving image, when an action is selected to move the Gaussian kernel at landmark 1511 by 1 mm, the Gaussian kernels at landmarks 1512 and 1513 are each moved by 0.72 mm and the Gaussian kernels at landmarks 1514 and 1515 are each moved by 0.26 mm. In the last stage, when the contour M is close to the contour F, the same action only causes the Gaussian kernel at landmark 1511 to move 1 mm.

In an advantageous implementation, a fixed step size can be used for action values on a pixel level (e.g., +/−1 pixel movements) that can be adjusted through the above described joint action method. The step size can be used to control convergence speed in contrast to precision. Bigger step sizes may be used in early deformations to roughly approach the fixed structure and then smaller step sizes can be used combined with smaller impact on the neighbors and joining less actions to reach a finer registration. In another possible implementation, adjusted step sizes may be applied in relation to the reward either using a fixed set of step sizes or using continuous action spaces. In the case of using principal components actions, which are either increasing or decreasing the components action values, a fixed number (e.g., +/−1) can be used to increase or decrease the components action values. As the action space can be large, and a greedy agent exploration scheme may be computationally inefficient and lead to long training times, sparse exploration schemes can be used. This can be achieved by applying a hierarchical approach on the parameters (multi-scale parameter representation). Different DNNs are trained with different step sizes. The first DNN with largest step size starts, the second takes over, and so on. Alternatively, an actor-critic architecture can be applied, where the actor (a first trained DNN) decides which action to take and the critic (a second trained DNN) evaluates the value of the action. This makes the training of continuous step sizes possible, as the two deep neural networks are trained iteratively, one to pick the action, the second one to choose the step size.

Various types of reward functions can be used for training the DNN. The reward function may be based on human-level recognition or may be a reward that is directly obtained from available ground truth deformation fields. Direct reward functions require the knowledge of the ground truth deformation field during training. As such ground truth data is not typically available for real medical image data, artificially generated deformation fields which are generated under controlled conditions can be used instead. In one embodiment, in the case of parametric deformation models, the distance of encoded components: $\|c_{gt}-c_{current}\|^2-\|c_{gt}-c_{next}\|^2$ can be directly used as the reward, where $c_{gt}$ is the ground truth encoded components or parameters of the deformation model.

Reward functions can also be designed based on human-level recognition, that is, the deformation is considered satisfactory when the image content (anatomic structures and boundaries) are well aligned. In one embodiment, the image difference: $-\Sigma|I_{ref}-I_{mov(t)}|^2$ can be used as the reward function. In another embodiment, landmark/mesh differences: $\Sigma\|P_{ref}-P_{mov(t)}\|^2$ can be used as the reward function, where $P_{ref}$ denotes a set of landmarks or mesh points in the reference image and $P_{mov(t)}$ denotes the set of landmarks or mesh points in the current moving image. In another embodiment, the image difference+the landmark/mesh differences: $\Sigma\|P_{ref}-P_{mov(t)}\|^2-\mu\Sigma|I_{ref}-I_{mov(t)}|^2$ can be used as the reward function, where $\mu$ is a weighting factor. In another embodiment, instead of the image difference, a deep learned similarity measure: $sim(I_{ref}-I_{mov(t)})$ can be used as the reward function.

Once the DNN is trained (in step 1000 of FIG. 10) to predict action values for the actions in the defined action space, the trained DNN is then used in the registration of newly received images. Returning the FIG. 10, at step 1002, first and second medical images are received. For example, the first and second medical images can be 2D or 3D images acquired using different imaging modalities (e.g., CT, MRI, ultrasound, PET, DynaCT, etc.), images of the same patient acquired at different times, or images acquired from different patients. The first and second medical images may be received directly from image acquisition devices, such as a CT scanner, MRI scanner, ultrasound device, C-arm image acquisition device, etc., or may be received by loading previously stored medical images from a memory or storage of a computer system or receiving the medical images in an electronic transmission from another computer system. One of the medical images is designated as the reference/fixed image $I_{ref}$ and the other is designated as the moving image $I_{mov}$.

A pre-processing stage may be performed before proceeding to step 1004. For example, one or more anatomical objects of interest (e.g., organs) can be segmented in each of the first and second medical images in order to define contours or meshes in the first and second images so that a contour or mesh in the moving image can be deformed to match the contour or mesh in the fixed image. A landmark or point of interest, such as a center of mass of an organ of interest, can be detected in each of the first and second images, and the first and second images can be initially aligned with respect to the point of interest.

At step 1004, action values for possible actions can be calculated based on the current state by the trained DNN. The trained DNN inputs the fixed image and the current moving image which is warped based on a current dense deformation field. In the first iteration, the current moving image is not yet warped. The trained DNN extracts features from the fixed and moving images, which provide an observation of the current state, and computes action-values for actions corresponding to adjustments of parameters in a parameter space of a deformation model used to encode the deformation of the moving image. The trained DNN may apply a probabilistic model to determine the action-values for the set of actions.

At step 1006, an action is selected based on the action-values calculated by the trained DNN. The action corresponds to an adjustment to a parameter in the parameter space of the deformation model used to encode the deformation of the moving image. The action with the highest predicted action-value may be selected.

At step 1008, a delta dense deformation field $\delta DF$ is computed based on the selected action and the deformable model used to encode the deformation of the moving image. The $\delta DF$ is a small dense deformation field corresponding to the selected action that provides an incremental adjustment to the overall deformation of the moving image. In one embodiment, when the deformation model used to encode the deformation of the moving image is a dense model that represents an entire deformation field of the moving image, the adjustment to the parameter in the parameter space of the deformation model corresponding to the selected action is performed and the change in the parameter space of the deformation model is decoded which maps the change in the parameter space of the deformation model to the $\delta DF$. In another embodiment, the deformation model used to encode the deformation of the moving image is a correspondence-based model that models deformation of landmark or control points of a structure of interest in the moving image. In this case, the adjustment to the parameter in the parameter space of the deformation model corresponding to the selected action is performed and the change is the parameter space of the deformation model is decoded, which maps the change in the parameter space of the deformation model to movement of the landmarks or control points to deform a contour or mesh of the structure of interest in the moving image. The $\delta DF$ for the entire moving image is then calculated from the deformation of the contour or mesh in the moving image, for example using interpolation and/or extrapolation.

At step 1010, the delta dense deformation field $\delta DF$ is applied to the moving image to warp the moving image. At step 1012, it is determined whether a stop condition has been met. For example, the stop condition can be met a predetermined maximum number of iterations has been performed, when the moving image converges, or when an error value between the fixed and moving images or between landmarks or mesh points in the fixed and moving images is less than a threshold value. If the stop condition has not yet been met, the method returns to step 1004 and repeats steps 1004-1012. Accordingly, the moving image is iteratively warped until the stop condition is met. When the stop condition is met, the method proceeds to step 1014.

At step 1014, the registration result is output. The registered first and second medical images (i.e., the fixed image and the final warped moving image) can be output by displaying the registered first and second medical images on a display of a computer system. The registered first and second medical images can be displayed in the same coordinate system. For example, the registered first and second images can be overlaid and displayed as a fused image. In addition to displaying the registered first and second images, the final dense deformation field used to warp the moving image, which is a composition of all the $\delta DFs$ applied to the moving image, can be visualized and displayed on the display of the computer system. The individual $\delta DFs$ applied to the moving image can also be visualized and displayed. The registered first and second medical images, as well as the final dense deformation field and/or the individual $\delta DFs$ can also be output by being electronically transmitting to a remote computer system to be displayed on a display of the remote computer system.

Although FIG. 10 only shows outputting the final registration result, it is also possible that the incremental registration results resulting from warping the moving image using the current dense deformation field can be output (e.g., displayed on a display of a computer system) as each iteration of steps 1004-1012 is performed. Such incremental results would allow a user to view each adjustment made by the intelligent artificial agent to the deformation of the moving image in real-time as the artificial agent iteratively warps the moving image to register the moving image to the fixed image.

As described above the point correspondence between the fixed and the moving images can be established using a ray-shooting algorithm that, given a segmentation mask of an object of interest shoots rays from the center of mass of the object to the surface with equal angular distances and selects the points where the rays leave the segmentation mask and landmark positions. This ray-shooting algorithm can be performed in the pre-processing phase prior to performing the registration. As these landmarks are not anatomically distinct points and are more utilized as regions for which actions can be selected by the trained DNN, this approach can be extended to shoot rays multiple times for the same landmark region with slightly varying angles from the center. That is, in a possible embodiment, the registration using the method of FIG. 10 can be performed multiple times using different landmarks acquired by ray-shooting with different angles to drive the registration to provide better representation of the shape of the object of interest in between the original landmark locations. The registration results from the various registrations can then be combined.

After running the registration process individually for each set of landmarks, multiples of the number of landmarks can be retrieved as point correspondences, which can result in a more accurate registration.

Hierarchical Deformable Registration Using Higher Resolution Image Patches.

Figure 16:
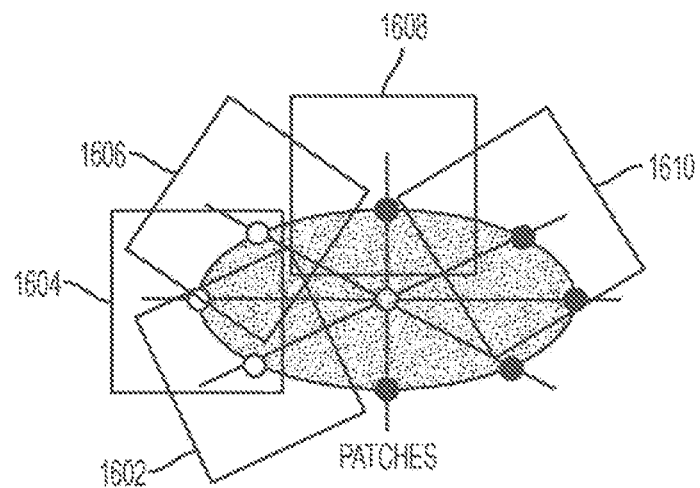
FIG. 16 illustrates patch extraction from landmark positions of a moving image.

In an advantageous embodiment, in order to increase the registration accuracy a hierarchical (multi-stage) framework based on higher resolution image patches may be utilized to perform deformable image registration. The first stage of the multi-stage deformable image registration method is performed on the full moving and fixed images using a first trained DNN. For example, the first stage can be performed as describe above in the method of FIG. 10. A second stage performs refinement then performs refinement of the registration estimated in the first stage based on higher resolution image patches extracted from the fixed and moving images using a second trained DNN. After the first stage registration on the full moving and fixed images, patches centered at the new landmark positions of the moving image are extracted from higher resolution versions of the fixed image and the current moving image. For example the higher resolution versions of the fixed and moving images can high-resolution images generated by up-sampling the fixed and moving images. Alternatively, the first stage can be performed on reduced resolution fixed and moving images generated by down-sampling the fixed and moving images acquired from the image acquisition devices, and the higher resolution versions are the original resolution fixed and moving images acquired from the image acquisition devices. FIG. 16 illustrates patch extraction from landmark positions of the moving image. As shown in FIG. 16, patches 1602, 1604, 1606, 1608, and 1610 are extracted at landmark locations in the moving image. Each of the image patches 1602, 1604, 1606, 1608, and 1610 is centered at the respective landmark and is oriented to be aligned with a normal of the contour at the respective landmark location. The image patches are extracted from the same locations in the fixed image.

Figure 17:
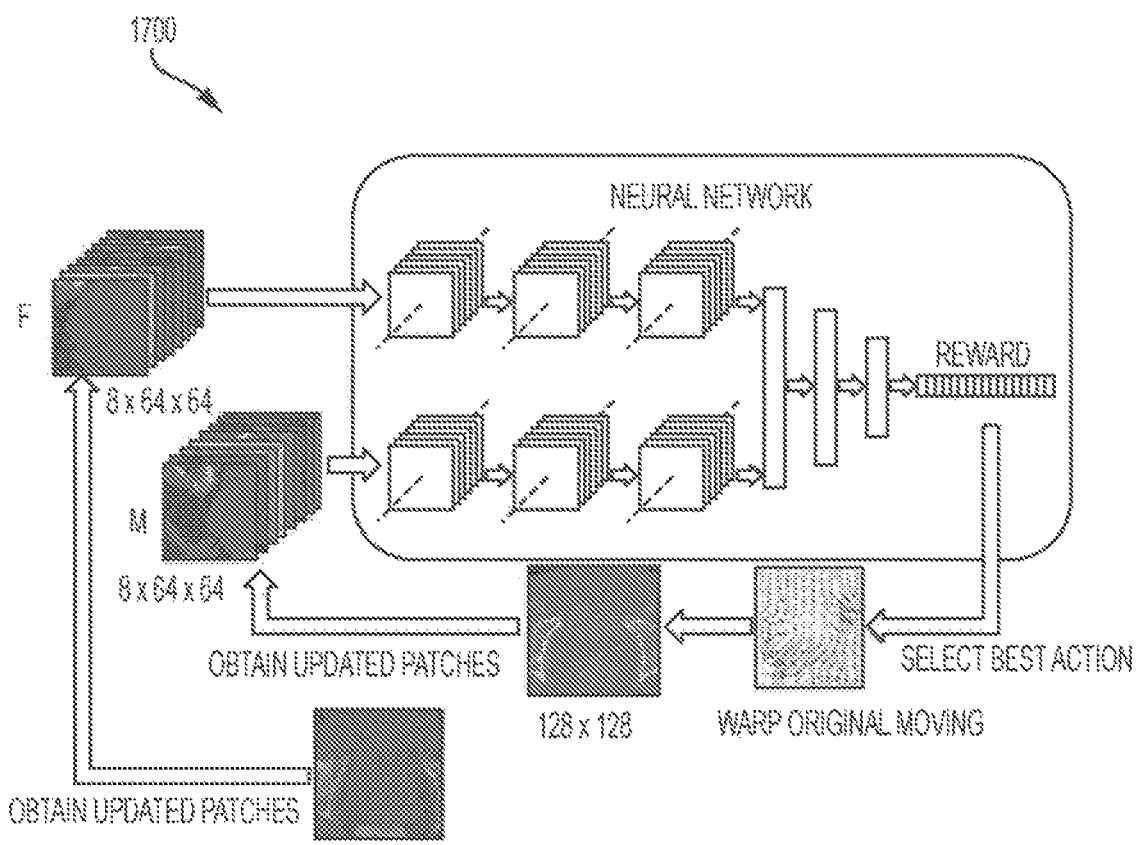
FIG. 17 illustrates a framework for performing a second stage of a multi-stage deformable registration according to an embodiment of the present invention.

FIG. 17 illustrates a framework for performing the second stage of the multi-stage deformable registration according to an embodiment of the present invention. As shown in FIG. 17, the image patches (F) extracted from the higher resolution fixed image and the image patches (M) extracted from the higher resolution moving image are input to a trained DNN 1700. All of the patches are input to the DNN 1700 in different channels. The deformation model, reward system, and action definitions can stay the same as in the first stage. However, the image warping is executed on a higher resolution. As the network is likely slower due to patch extraction, multiple channels, and higher resolution warping, in an advantageous embodiment, the method of FIG. 17 is used as a refinement step after the first stage is used to perform rough registration. The DNN 1700 extracts features from the input higher resolution image patches and calculates rewards for the set of actions. The best action is selected and the higher resolution moving image is warped based on the selected action, which results in movement of one or more of the landmark positions. Updated image patches are obtained from the higher resolution moving image at the locations of the updated landmark locations in the moving image, and updated image patches at the same locations are obtained from the higher resolution fixed image. This process then repeats until a stop condition is reached. The step size for the actions can also be increased to reduce the number of steps at the higher resolution or decreased to reach a higher accuracy.

Figure 18:
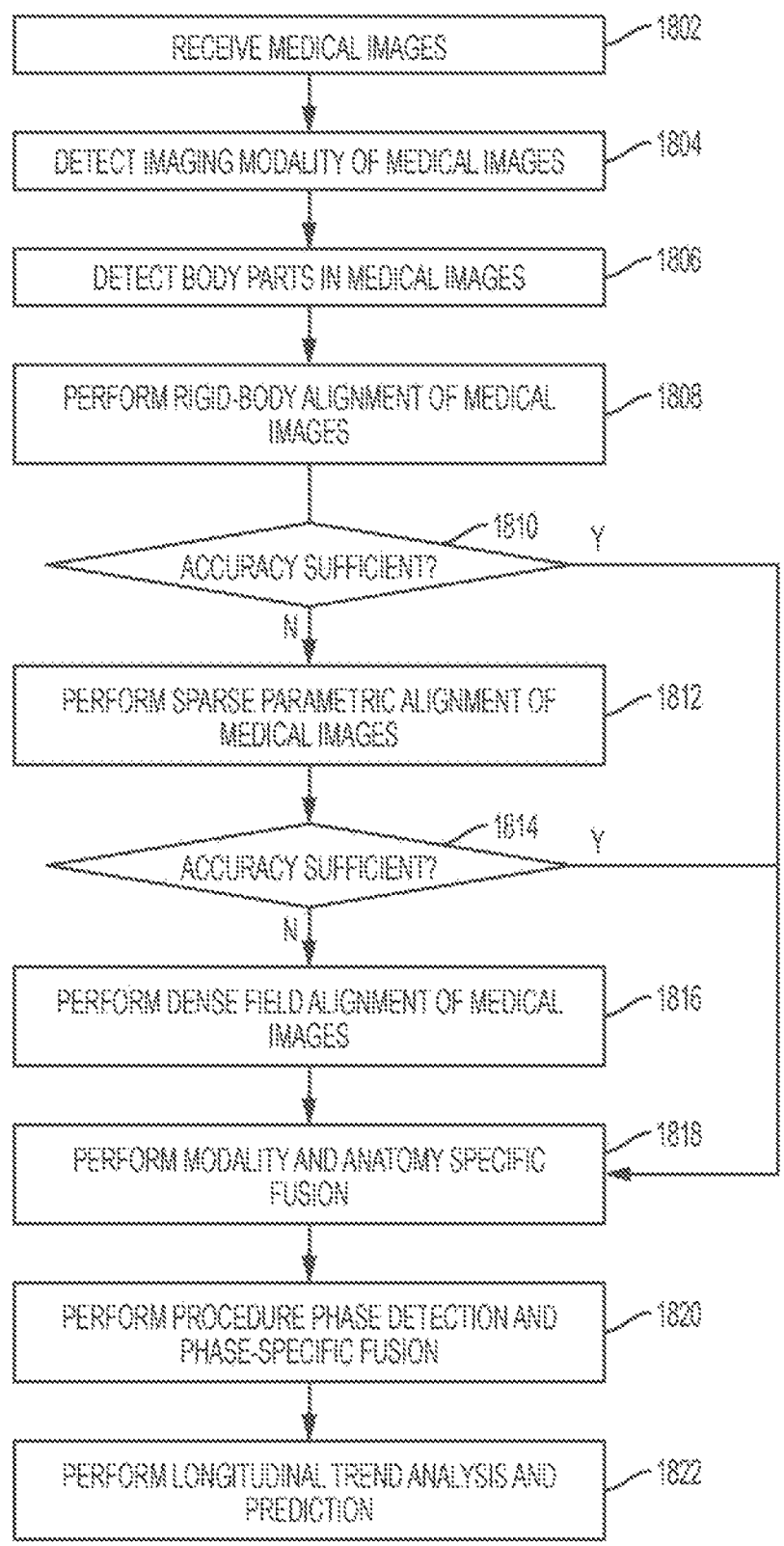
FIG. 18 illustrates a method of autonomous intelligent artificial agent based cognitive image fusion according to an embodiment of the present invention.

Clinical Workflow for Autonomous Artificial Intelligence Based Image Registration Due to the vast number of applications to which image fusion/registration can be applied, it is challenging to develop a general method that works robustly for all cases. According to an advantageous embodiment of the present invention, various trained intelligent artificial agents can be used to autonomously implement a clinical workflow that recognizes the registration task or tasks to be performed to achieve fusion of two or more medical images without the need of user interaction. FIG. 18 illustrates a method of autonomous artificial intelligence (AI)-based image registration according to an embodiment of the present invention. The method of FIG. 18 utilizes various intelligent artificial agents to perform various tasks related to image registration. Each intelligent artificial agent is implemented by one or more processors of one or more computer systems executing computer program instructions defining operations the artificial agent. In order to perform its designated task, each artificial agent autonomously observes a state of its environment and performs actions learned via artificial intelligence/machine learning techniques.

At step 1802, two or more medical images to be fused are received. The medical images may be 2D or 3D images acquired using any medical imaging modality. The medical images may be received directly from one or more medical image acquisition devices, received by loading previously stored medical images from a memory or storage of a computer system, or received via one or more electronic transmissions from a remote computer system.

At step 1804, an imaging modality is detected for each of the medical images to be fused. A trained intelligent artificial agent automatically detects the imaging modality (e.g., CT, MRI, Ultrasound, DynaCT, PET, etc.) for each image to be fused. In an exemplary implementation, the trained artificial agent can utilize one or more trained deep neural networks (DNN) to detect the imaging modalities of the medical images.

At step 1806, body parts are detected in each of the medical images to be fused. For each image, a trained intelligent artificial agent corresponding to the imaging modality detected for that agent automatically detects a region of the body (e.g., cardiac, abdominal, head, full body, etc.) present in that image. In an alternative implementation, it is possible that an intelligent artificial agent can be trained to perform the modality and the body region detection in the same step. In addition to detecting the body region present in each image, a trained artificial agent corresponding to the detected body region and imaging modality can be used to detect and/or segment specific anatomical structures, such as organs, vessels, landmarks, etc. in each image. For example, a trained artificial agent may use deep learning based segmentation.

At step 1808, rigid-body alignment of the medical images is performed by a trained artificial agent. In particular, for a given pair of images (or given configuration of multiple images), a trained artificial agent corresponding to the right configuration (i.e., imaging modality and anatomy) aligns the images by performing rigid-body registration of the images, as described above in the embodiment FIG. 5. Multiple intelligent artificial agents can be trained using supervised deep reinforcement learning as described above, each trained to perform rigid-body registration for a different configuration of imaging modality and anatomy. In a possible implementation, the medical images can be down-sampled to generate reduced-resolution images can the rigid registration can be performed based on the reduced-resolution images for fast alignment.

At step 1810, an accuracy analysis of the alignment is performed and it is determined whether the accuracy of the alignment is sufficient. A trained artificial agent can evaluate the accuracy of the alignment and assign an accuracy measure or confidence value to the alignment. The trained artificial agent may also be trained to consider whether the alignment would be improved by deformable registration. If the accuracy of the alignment is determined to be sufficient, the method proceeds to step 1818. If the accuracy of the alignment is determined to be insufficient and considered to be improvable by deformable registration, the method proceeds to step 1812.

At step 1812, sparse parametric alignment of the medical images is performed by a trained artificial agent. In particular, a trained artificial agent corresponding to the right configuration (i.e., imaging modality and anatomy) can perform the sparse deformable image registration of the medical images using the method of FIG. 10 with a sparse parametric deformation model. For example, a thin plate spline (TPS) model can be used as the deformation model. The trained artificial agent can be trained using supervised trajectory learning, as described above, with the movement (action) in each step corresponding to movement of one of the TPS control points. The total maximum movement of a TPS control point can be constrained since rigid-body alignment is performed beforehand.

At step 1814, an accuracy analysis of the alignment is performed and it is determined whether the accuracy of the alignment is sufficient. A trained artificial agent can evaluate the accuracy of the alignment and assign an accuracy measure or confidence value to the alignment. The trained artificial agent may also be trained to consider whether the alignment would be improved by dense deformable registration. If the accuracy of the alignment is determined to be sufficient, the method proceeds to step 1818. If the accuracy of the alignment is determined to be insufficient and considered to be improvable by dense deformable registration, the method proceeds to step 1816.

At step 1816, dense field alignment of the medical images is performed by a trained artificial agent. In one embodiment, a trained artificial agent corresponding to the right configuration (i.e., imaging modality and anatomy) can perform the sparse deformable image registration of the medical images using the method of FIG. 10 with a dense deformation model. Although not shown in FIG. 18, in a possible implementation, a final alignment accuracy evaluation may be performed by a trained artificial agent before proceeding to step 1818.

At step 1818, modality and anatomy specific fusion is performed for the aligned medical images. A trained intelligent artificial agent fuses the information from all of the images using learned proper visualization and quantification methods according to the detected modality, anatomy, and alignment accuracy. For example, the trained artificial agent can tune cinematic rendering based on the fused knowledge for hyper-realistic accuracy. Data enhancement can be achieved by the trained artificial agent selecting, for each voxel, which information (from which of the aligned medical images) to show, such as an ultrasound image with scar tissue highlighted.

At step 1820, procedure phase detection and phase-specific fusion are performed. A trained intelligent artificial agent detects the phase of the procedure (e.g., surgery/intervention) based on the medical images and fuses information associated with the current phase in the aligned medical images.

At step 1822, longitudinal trend analysis and prediction are performed. A trained intelligent artificial agent learns trends from longitudinal data and predicts a next step to guide the procedure based on the learned trends.

According to an advantageous implementation, a "master" intelligent artificial agent can be trained to control the workflow of FIG. 18. Various trained artificial agents for various registration tasks and various modality/anatomy configurations can be stored in one or more databases on a storage device of a computer system or networked "cloud"-based storage. The master intelligent artificial agent is trained to determine which other trained intelligent artificial agents are retrieved to perform the various steps of the method of FIG. 18.

Direct Regression of Regression Parameters

In the above described embodiments, in order to perform registration of medical images, artificial agents use trained DNNs to iteratively select actions that adjust the transformation parameters. In an alternative embodiment, medical image registrations can be performed using a DNN that is trained to directly regress the transformation parameters given two (or more) input images to be registered. In this case, instead of iteratively selecting registration actions, the first and second images (i.e., fixed and moving images) are input into the trained DNN and the trained DNN directly outputs the transformation parameters that register the moving image to the fixed image. In an exemplary implementation, for a parametric transformation (e.g., rigid transformation, affine transformation, or parametric deformation), a deep neural network for regression can be trained based on training pairs with known ground truth transformations with the loss function being calculated on the transformation parameters. In another exemplary implementation, for dense deformation fields, a deep encoder-decoder can be trained based on trained pairs with known ground truth transformations to directly output the deformation field. A method for training such a deep neural network using weakly supervised deep dense correspondence learning is described below.

Deformable Image Registration Using Weakly Supervised Deep Dense Correspondence Learning Deep Learning methods typically require a large number of labeled images to supervise the training, and such data is often not available and difficult to obtain for deformable image registration (i.e., estimating dense correspondence between images). Specifically, the "label" for deformable image registration is a dense vector field, which is very difficult to manually annotate. In an advantageous embodiment of the present invention, cycle consistency of dense correspondences among multiple images is exploited to supervise deep dense correspondence learning for deformable image registration without the need for manually annotated labels.

Figure 19:
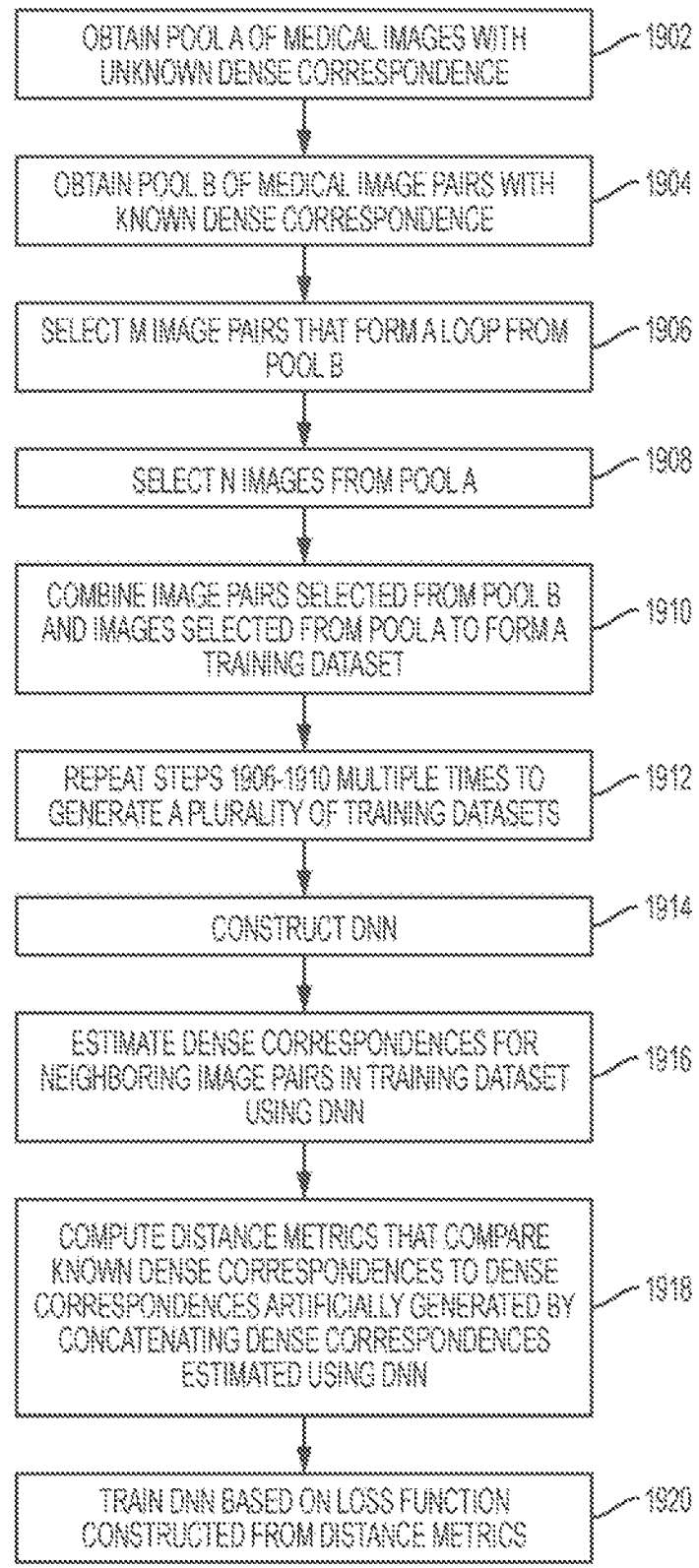
FIG. 19 illustrates a method of training a DNN for deformable image registration using weakly supervised deep dense correspondence learning according to an embodiment of the present invention.

FIG. 19 illustrates a method of training a deep neural network (DNN) for deformable image registration using weakly supervised deep dense correspondence learning according to an embodiment of the present invention. At step 1902, a first pool (A) of medical images with unknown dense correspondence is obtained. The medical images in pool A can be obtained from a database of stored medical images. Alternatively, the medical images in pool A can be obtained by acquiring images using an image acquisition device. The medical images in pool A can be any type of medical images depending on a registration task for which the DNN is being trained.

At step 1904, a second pool (B) of medical image pairs with known dense correspondence is obtained. The medical image pairs can be acquired using one or more image acquisition devices or can be obtained from a database of stored medical images. The size of pool B will likely be much smaller than the data pool (A) with unknown dense correspondence. Various techniques can be used to obtain the dense correspondence between the medical image pairs in pool B. In one possible implementation, the dense correspondence between the medical image pairs can be manually annotated. In another possible implementation, one medical image can be artificially deformed via a deformation model, such as a spline model, statistical model biomechanical model, etc. The original image and the deformed image form a pair with a known dense correspondence. In another possible implementation, image pairs can from the same patient can be acquired with a certain motion tracking method that provides the dense correspondence between the images. For example, tagged cardiac MRIs, or CT/MR images acquired with respiratory and/or cardiac phase recorded as a surrogate signal of the underlying motion can be used to obtain paired images with known dense correspondence.

At step 1906, M image pairs that form a loop are selected from pool B. For example, image pairs $(I_a, I_b)$, $(I_b, I_c)$, $(I_c, I_a)$ can be selected from pool B if M=3. The dense correspondences for the selected image pairs $(I_a, I_b)$, $(I_b, I_c)$, $(I_c, I_a)$ are denoted as $F_{ab}, F_{bc}, F_{ca}$, respectively. The image pairs can be picked randomly. M can be any integer greater than 1. In an exemplary implementation, M=3 and the method of FIG. 19 is described using the example of M=3.

At step 1908, N images are selected from pool A. The N images selected from pool A are referred to as $I_1, I_2, \ldots, I_N$. These images can be selected randomly from pool A.

At step 1910, the image pairs selected from pool B and the images selected from pool A are combined to form a training dataset. In particular, the images from pool B and pool A are combined and order as $I_a, I_1, \ldots, I_k, I_b, I_{k+1}, \ldots, I_j, I_c, I_{j+1}, \ldots, I_N$. The images $I_a, I_1, \ldots, I_k, I_b, I_{k+1}, \ldots, I_j, I_c, I_{j+1}, \ldots, I_N$ and the dense correspondences $F_{ab}, F_{bc}, F_{ca}$ form one training dataset.

At step 1912, steps 1906-1910 are repeated multiple times to generate a plurality of training datasets. Each of these training datasets formed by combining the image pairs selected from pool B and the images selected from pool A is treated as a single training example for training the DNN. Accordingly, in an advantageous implementation, steps 1906-1910 are repeated a large number of times to generate a large number of training datasets (training examples).

Figure 20:
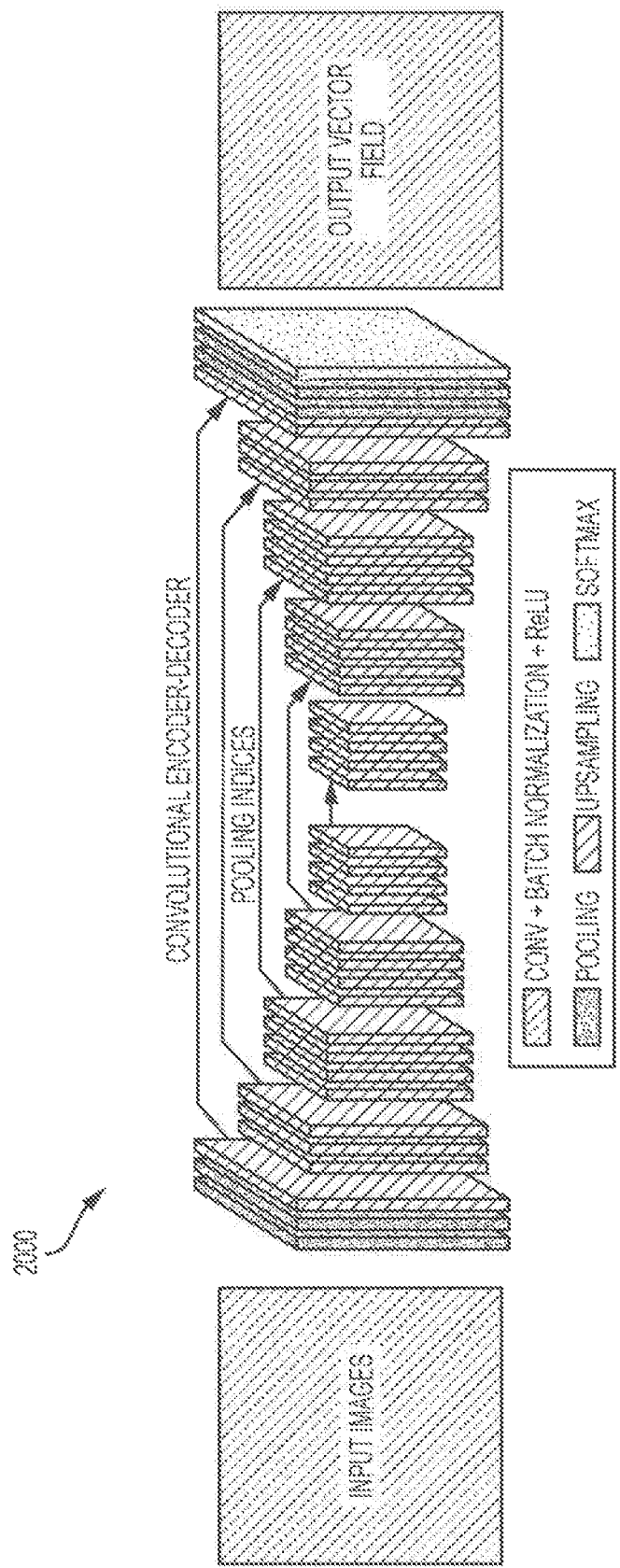
FIG. 20 illustrates an exemplary network architecture for a Convolutional Encoder-Decoder Network for dense correspondence estimation.
Figure 21:
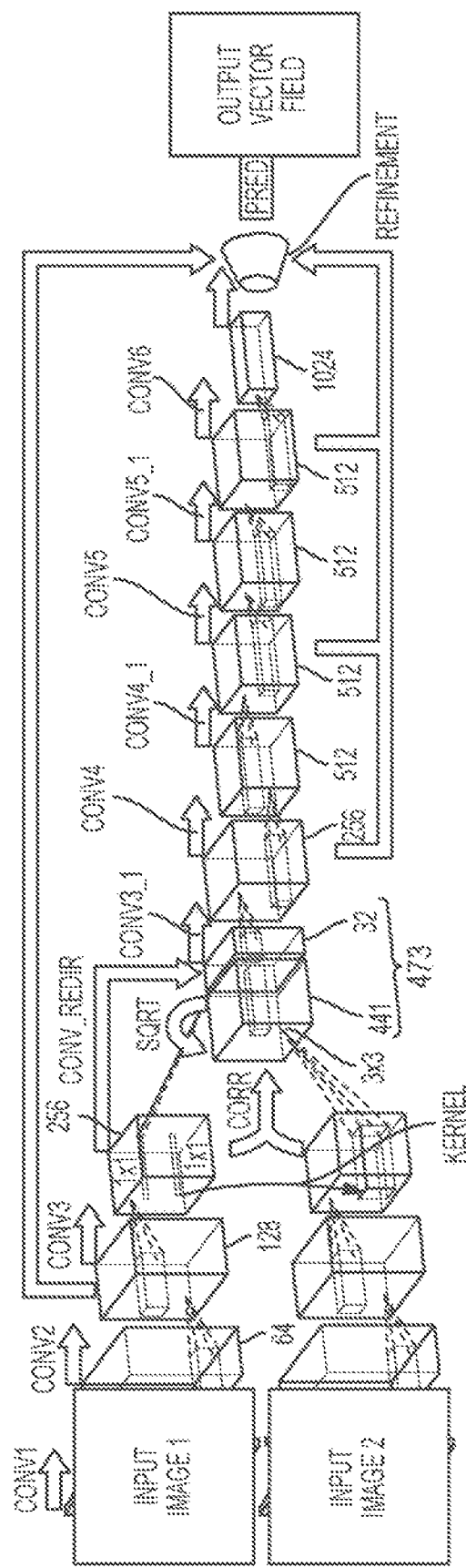
FIG. 21 illustrates an exemplary Flow-Net like deep architecture for dense correspondence estimation.

At step 1914, a deep neural network (DNN) is constructed. In particular, a DNN is constructed that takes two images an input, and outputs a 3D vector field, which represents the dense correspondence between the two input images. In one embodiment, the DNN can be a Convolutional Encoder-Decoder Network. FIG. 20 illustrates an exemplary network architecture for Convolutional Encoder-Decoder Network 2000 for dense correspondence estimation. In another embodiment, the DNN can use a FlowNet-like architecture. FIG. 21 illustrates an exemplary FlowNet-like deep architecture 2100 for dense correspondence estimation. Other types of DNN architectures can be used as well. The DNN is denoted as $F_W(\cdot,\cdot)$, where W denotes the weights of the DNN that are learned in training.

Returning to FIG. 19, at step 1916, for each training dataset, dense correspondences are estimated for each neighboring pair of images in the training dataset. For a given training dataset, the DNN is applied on every neighboring pair of images in $I_a, I_1, \ldots, I_k, I_b, I_{k+1}, \ldots, I_j, I_c, I_{j+1}, \ldots, I_N$), resulting in estimated an estimated dense correspondence being calculated by the DNN for each neighboring image pair in the training dataset, i.e., $F_W(I_a, I_1), F_W(I_1, I_2), \ldots, F_W(I_{N-1}, I_N), F_W(I_N, I_a)$. The first and last images in the training dataset $I_a$ and $I_N$, respectively, are considered to be neighboring.

At step 1918, distance metrics are computed to compare the known dense correspondences for the image pairs selected from pool B in each training dataset to dense correspondences artificially generated by concatenating the dense correspondences estimated by the DNN. In a given training dataset, the dense correspondences estimated for the neighboring image pairs by the DNN in step 1916 can be concatenated to artificially generate dense correspondences for the image pairs $(I_a, I_b)$, $(I_b, I_c)$, $(I_c, I_a)$ selected from pool B in the training dataset. In particular, the artificially generated dense correspondence for $(I_a, I_b)$ can be calculated by concatenating the estimated dense correspondences for the neighboring image pairs from $I_a$ to $I_b$, $F_W(I_a, I_1), F_W(I_1, I_2), \ldots, F_W(I_{k-1}, I_k), F_W(I_k, I_b)$. The artificially generated dense correspondence for $(I_b, I_c)$ can be calculated by concatenating the estimated dense correspondences for the neighboring image pairs from $I_b$ to $I_c$, $F_W(I_b, I_{k+1}), F_W(I_{k+1}, I_{k+2}), \ldots, F_W(I_{j-1}, I_j), F_W(I_j, I_c)$. The artificially generated dense correspondence for $(I_c, I_a)$ can be calculated by concatenating the estimated dense correspondences for the neighboring image pairs from $I_c$ to $I_a$, $F_W(I_c, I_{j+1}), F_W(I_{j+1}, I_{j+2}), \ldots, F_W(I_{N-1}, I_N), F_W(I_N, I_a)$. Distance metrics are calculated to compare to known dense correspondences $F_{ab}, F_{bc}, F_{ca}$ for $(I_a, I_b)$, $(I_b, I_c)$, $(I_c, I_a)$ with the artificially generated dense correspondences for $(I_a, I_b)$, $(I_b, I_c)$, $(I_c, I_a)$:

$$D_{ab} = D(F_{ab}, (F_W(I_a, I_1), F_W(I_1, I_2), \ldots, F_W(I_{k-1}, I_k), F_W(I_k, I_b)))$$

$$D_{bc} = D(F_{bc}, (F_W(I_b, I_{k+1}), F_W(I_{k+1}, I_{k+2}), \ldots, F_W(I_{j-1}, I_j), F_W(I_j, I_c)))$$

$$D_{ca} = D(F_{ca}, (F_W(I_c, I_{j+1}), F_W(I_{j+1}, I_{j+2}), \ldots, F_W(I_{N-1}, I_N), F_W(I_N, I_a)))$$

At step 1920, the DNN is trained based on a loss function constructed from the distance metrics. If the dense correspondences produced by the DNN are correct, i.e., they represent the real correspondences between the images, the concatenated dense correspondence between two images should be the same as the real dense correspondence. This property is referred to as Cycle Consistency. The distance metrics $D_{ab}, D_{bc}, D_{ca}$ are used to construct the loss function for training the DNN. For example, the loss function can be a linear combination of $D_{ab}, D_{bc}, D_{ca}$. The DNN is then trained (e.g., using backpropagation and gradient descent techniques) to learn weights that minimize the loss function over all of the training datasets.

Figure 22:
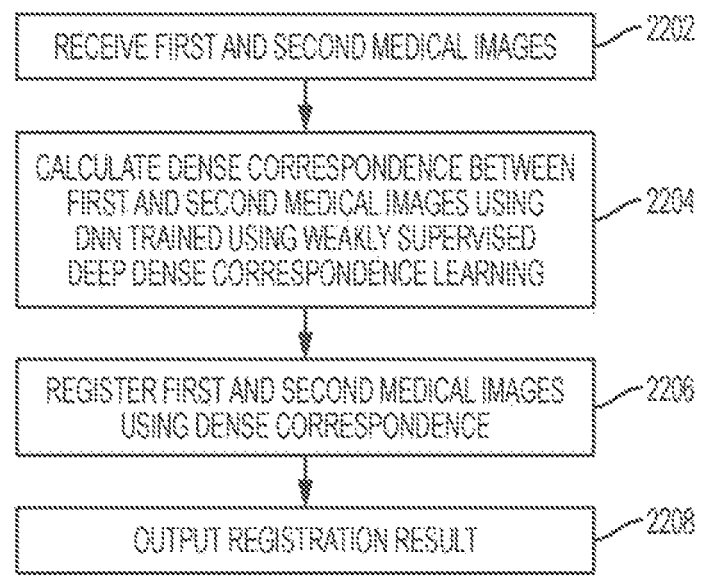
FIG. 22 illustrates a method for deformable registration of medical images according to an embodiment of the present invention.

FIG. 22 illustrates a method for deformable registration of medical images according to an embodiment of the present invention. At step 2202, first and second medical images are received. At step 2204, a DNN trained using weakly supervised deep dense correspondence learning calculates a dense correspondence between the first and second medical images. In particular, the first and second medical images are input to a DNN trained using the method of FIG. 19, and the trained DNN outputs a 3D vector field representing the dense correspondence (i.e., dense deformation field) between the first and second images. At step 2206, the first and second medical images are registered using the dense correspondence. For example, the first image can be registered to the second image by warping the first medical image using the dense correspondence between the first and second medical images. At step 2208, registration result is output, for example, by displaying the registered first and second images on a display of a computer system.

The above described methods for intelligent agent based image registration can be applied to many different medical image registration applications. Various registrations applications for which the above described methods for intelligent agent based image registration can be advantageously applied are described herein. It is to be understood that the above described methods are not limited to these examples and may be applied for other medical imaged registrations applications as well.

In one embodiment, the above described methods for intelligent agent based image registration may be applied to perform fusion of ultrasound and volumetric cardiac images (e.g., MR or CT) for joint function, flow, anatomy, and coronary assessment. Previous registrations techniques require explicitly defining a segmentation of a coronary structure (e.g., full heart, chamber(s), valve) or anatomical landmarks. The above described methods enable the fusion of ultrasound and volumetric cardiac image (e.g., MR or CT) without the need to explicitly define a segmentation or landmarks.

In another embodiment, the above described methods of intelligent agent based image registration may be applied to register CT or MR images to ConeBeam CT images. Interventional ConeBeam CT is often used to guide surgeries or interventions (e.g., cardiac interventions, spine surgery, etc.). Interventional ConeBeam CT often suffers from image artifacts dues to device, which makes robust image registration difficult using previous registration techniques. The above described methods provides robust registration of CT or MR images to Conebeam CT images even in images with noise or image artifacts, which allows to image data from the pre-operative CT or MR images to be fused with the interventional ConeBeam CT images used for guiding an intervention or surgical procedure.

In another embodiment, the above described methods of intelligent agent based image registration may be applied to perform automatic change detection through deformable registration. For example, a previously acquired medical image of a patient and a follow-up medical image of the same patient can be registered using the above described methods for intelligent agent based deformable image registration in order to determine a deformation field that shows changes to the anatomy of the patient over time. Such automatic change detection can be used in cancer screening to detect tumor growth or reduction over time, to track changes in stenoses, plaques, or other abnormalities in coronary arteries or other vessels, or to track changes in any other anatomical structure of patient due to disease or treatment.

In another embodiment, the above described methods for intelligent agent based image registration can be used to perform motion compensation. For example, when registering a pre-operative medical image (e.g., CT or MR) to intraoperative/interventional medical images acquired during a procedure, a trained intelligent artificial agent for image registration can be kept always running in a perpetual state as real-time interventional medical images are acquired and the images are always registered even when movement occurs in the real-time interventional images (e.g., due to patient movement, respiratory motion, or cardiac motion). Using the above described methods, the intelligent artificial agent automatically re-registers the images as the interventional medical images are received in real-time, such that the registration immediately "catches up" to the movement in the real-time images, thus allowing for real-time perpetual compensation of respiratory motion.

Figure 23:
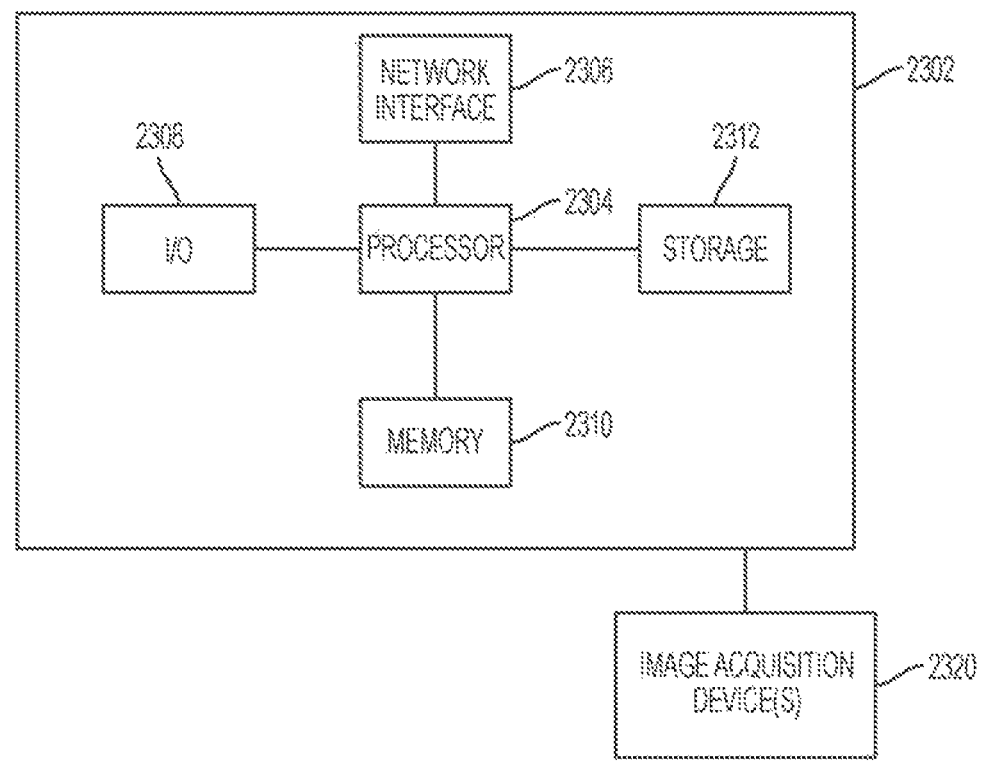
FIG. 23 is a high-level block diagram of a computer capable of implementing the present invention.

The above-described methods for intelligent agent based image registration can be implemented on one or more computers using well-known computer processors, memory units, storage devices, computer software, and other components. A high-level block diagram of such a computer is illustrated in FIG. 23. Computer 2302 contains a processor 2304, which controls the overall operation of the computer 2302 by executing computer program instructions which define such operation. The computer program instructions may be stored in a storage device 2312 (e.g., magnetic disk) and loaded into memory 2310 when execution of the computer program instructions is desired. Thus, the method steps illustrated in FIGS. 2, 3, 4, 5, 6, 7, 10, 12, 14, 17, 18, 19, and 22 may be defined by the computer program instructions stored in the memory 2310 and/or storage 2312 and controlled by the processor 2304 executing the computer program instructions. One or more image acquisition devices 2320, such as a CT scanning device, C-arm image acquisition device, MR scanning device, Ultrasound device, etc., can be connected to the computer 2302 to input image data to the computer 2302. It is possible that the computer and one or more of the image acquisition devices 2320 may be implemented as one device. It is also possible that the image acquisition devices 2320 and the computer 2302 communicate wirelessly through a network or wireless communication protocol. In a possible embodiment, the computer 2302 may be located remotely with respect to the image acquisition devices 2320 and may perform some or all of the method steps of FIGS. 2, 3, 4, 5, 6, 7, 10, 12, 14, 17, 18, 19, and 22 as part of a server or cloud based service. The computer 2302 also includes one or more network interfaces 2306 for communicating with other devices via a network. The computer 2302 also includes other input/output devices 908 that enable user interaction with the computer 2302 (e.g., display, keyboard, mouse, speakers, buttons, etc.). One skilled in the art will recognize that an implementation of an actual computer could contain other components as well, and that FIG. 9 is a high level representation of some of the components of such a computer for illustrative purposes.

The above described methods for intelligent artificial agent based image registration and/or training deep neural networks may be implemented in network-based cloud computing system. In such a network-based cloud computing system, a server communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. Certain steps of the above described methods may be performed by a server or by other computers/processors in the network-based cloud-computing system. Certain steps of the above described methods may be performed locally by a client computer in a network-based cloud computing system. The steps of the above described methods for intelligent artificial agent based image registration and/or training deep neural networks may be implemented in network-based cloud computing system may be performed by the network-based cloud-computing system or by a local client computer in any combination. In one embodiment, one or more trained artificial intelligent agents are stored on a server or other remote computer device in the network-based cloud-computing system, and a client computer electronically transmits two or more medical images to be registered to the server of the network-based cloud-computing system. The server and/or other computers/processors in the network-based cloud-computing system performs the registration of the medical images using the one or more trained artificial agents and electronically transmits the registration results to the client computer, which then displays the registration results on a display of the client computer. The method steps to perform the registration in the network-based cloud-computing system can be performed by a single computer device in the network-based cloud-computing system (e.g., the server) or may be distributed on multiple computer devices or processors in the network-based cloud-computing system.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for deformable registration of medical images using an intelligent artificial agent, comprising:
    receiving a first medical image and a second medical image;
    calculating action-values for a plurality of actions based on a current state using a trained deep neural network, the current state determined from the first medical image and the second medical image;
    selecting an action from the plurality of actions based on the calculated action-values;
    computing a deformation field based on the selected action and a deformation model;
    applying the deformation field to the first medical image to warp the first medical image; and
    repeating the calculating, the selecting, the computing, and the applying for a plurality of iterations using the warped first medical image as the first medical image to register the first medical image and the second medical image.

2. The method of claim 1, wherein calculating action-values for a plurality of actions based on a current state using a trained deep neural network comprises:
    extracting features from the first medical image using first convolutional layers of the trained deep neural network;
    extracting features from the second medical image using second convolutional layers of the trained deep neural network; and
    comparing the extracted features from the first medical image and the extracted features from the second medical image to calculate the action-values for the plurality of actions.

3. The method of claim 2, wherein the first convolutional layers and the second convolutional layers are implemented with separate weights.

4. The method of claim 1, wherein computing a deformation field based on the selected action and a deformation model comprises:
    encoding deformation for an entirety of the first medical image using a dense model.

5. The method of claim 4, wherein applying the deformation field to the first medical image to warp the first medical image comprises:
    decoding the deformation for the entirety of the first medical image; and
    applying the decoded deformation to the first medical image.

6. The method of claim 1, wherein computing a deformation field based on the selected action and a deformation model comprises:
    encoding deformation at particular points in the first medical image that have corresponding points in the second medical image using a correspondence based model.

7. The method of claim 6, wherein applying the deformation field to the first medical image to warp the first medical image comprises:
    decoding the deformation at the particular points in the first medical image;
    transforming a mesh of a segmented structure in the first medical image based on the decoded deformation;
    computing a dense deformation field based on the transformation of the mesh; and
    applying the computed dense deformation field to the first medical image.

8. The method of claim 1, wherein computing a deformation field based on the selected action and a deformation model comprises:
    modeling deformation of pixels at a location in the first medical image as having a Gaussian distribution; and
    computing a deformation at a particular point in the first medical image based on a distance between the particular point and the location, a magnitude of the Gaussian distribution, and a standard deviation of the Gaussian distribution.

9. The method of claim 1, wherein the trained deep neural network is trained to predict the action-values for the plurality of actions based on a plurality of training image pairs with known ground truth transformation parameters using reinforcement learning in which, for each training image pair, a reward for each action of the plurality of actions at a given state is used to train the deep neural network to learn an optimal registration policy.

10. An apparatus for deformable registration of medical images using an intelligent artificial agent, comprising:
    means for receiving a first medical image and a second medical image;
    means for calculating action-values for a plurality of actions based on a current state using a trained deep neural network, the current state determined from the first medical image and the second medical image;
    means for selecting an action from the plurality of actions based on the calculated action-values;
    means for computing a deformation field based on the selected action and a deformation model;
    means for applying the deformation field to the first medical image to warp the first medical image; and
    means for repeating the calculating, the selecting, the computing, and the applying for a plurality of iterations using the warped first medical image as the first medical image to register the first medical image and the second medical image.

11. The apparatus of claim 10, wherein the means for calculating action-values for a plurality of actions based on a current state using a trained deep neural network comprises:
  means for extracting features from the first medical image using first convolutional layers of the trained deep neural network;
  means for extracting features from the second medical image using second convolutional layers of the trained deep neural network; and
  means for comparing the extracted features from the first medical image and the extracted features from the second medical image to calculate the action-values for the plurality of actions.

12. The apparatus of claim 11, wherein the first convolutional layers and the second convolutional layers are implemented with separate weights.

13. The apparatus of claim 10, wherein the means for computing a deformation field based on the selected action and a deformation model comprises:
  means for encoding deformation for an entirety of the first medical image using a dense model.

14. The apparatus of claim 13, wherein the means for applying the deformation field to the first medical image to warp the first medical image comprises:
  means for decoding the deformation for the entirety of the first medical image; and
  means for applying the decoded deformation to the first medical image.

15. A non-transitory computer readable medium storing computer program instructions for deformable registration of medical images using an intelligent artificial agent, the computer program instructions defining operations comprising:
  receiving a first medical image and a second medical image;
  calculating action-values for a plurality of actions based on a current state using a trained deep neural network, the current state determined from the first medical image and the second medical image;
  selecting an action from the plurality of actions based on the calculated action-values;
  computing a deformation field based on the selected action and a deformation model;
  applying the deformation field to the first medical image to warp the first medical image; and
  repeating the calculating, the selecting, the computing, and the applying for a plurality of iterations using the warped first medical image as the first medical image to register the first medical image and the second medical image.

16. The non-transitory computer readable medium of claim 15, wherein calculating action-values for a plurality of actions based on a current state using a trained deep neural network comprises:
  extracting features from the first medical image using first convolutional layers of the trained deep neural network;
  extracting features from the second medical image using second convolutional layers of the trained deep neural network; and
  comparing the extracted features from the first medical image and the extracted features from the second medical image to calculate the action-values for the plurality of actions.

17. The non-transitory computer readable medium of claim 15, wherein computing a deformation field based on the selected action and a deformation model comprises:
  encoding deformation at particular points in the first medical image that have corresponding points in the second medical image using a correspondence based model.

18. The non-transitory computer readable medium of claim 17, wherein applying the deformation field to the first medical image to warp the first medical image comprises:
  decoding the deformation at the particular points in the first medical image;
  transforming a mesh of a segmented structure in the first medical image based on the decoded deformation;
  computing a dense deformation field based on the transformation of the mesh; and
  applying the computed dense deformation field to the first medical image.

19. The non-transitory computer readable medium of claim 15, wherein computing a deformation field based on the selected action and a deformation model comprises:
  modeling deformation of pixels at a location in the first medical image as having a Gaussian distribution; and
  computing a deformation at a particular point in the first medical image based on a distance between the particular point and the location, a magnitude of the Gaussian distribution, and a standard deviation of the Gaussian distribution.

20. The non-transitory computer readable medium of claim 15, wherein the trained deep neural network is trained to predict the action-values for the plurality of actions based on a plurality of training image pairs with known ground truth transformation parameters using reinforcement learning in which, for each training image pair, a reward for each action of the plurality of actions at a given state is used to train the deep neural network to learn an optimal registration policy.

* * * * *